(12) United States Patent
Allen et al.

(10) Patent No.: US 10,759,727 B2
(45) Date of Patent: Sep. 1, 2020

(54) PROCESSES TO CREATE MULTIPLE VALUE STREAMS FROM BIOMASS SOURCES

(71) Applicant: INTERCONTINENTAL GREAT BRANDS LLC, East Hanover, NJ (US)

(72) Inventors: Lloyd Allen, Vancouver (CA); Claudio Arato, Vancouver (CA); Terry Brix, Vancouver (CA); Peter Andrew Clarke, Reading (GB); Joshua Davies, Vancouver (CA); Bryan Gene, Vancouver (CA); Mark Kirby, Vancouver (CA); Quak Foo Lee, Vancouver (CA); William McKean, Vancouver (CA); Ankit Munjapara, East Hanover, NJ (US); Clive Richard Norton, East Hanover, NJ (US); Stuart A. Stein, East Hanover, NJ (US); Greg Stock, Bournville (GB); David Sugden, Reading (GB)

(73) Assignee: INTERCONTINENTAL GREAT BRANDS LLC, East Hanover, NJ (US)

( * ) Notice: Subject to any disclaimer, the term of this patent is extended or adjusted under 35 U.S.C. 154(b) by 0 days.

(21) Appl. No.: 16/075,394

(22) PCT Filed: Feb. 17, 2017

(86) PCT No.: PCT/US2017/018260
§ 371 (c)(1),
(2) Date: Aug. 3, 2018

(87) PCT Pub. No.: WO2017/143118
PCT Pub. Date: Aug. 24, 2017

(65) Prior Publication Data
US 2019/0039981 A1 Feb. 7, 2019

Related U.S. Application Data

(60) Provisional application No. 62/297,434, filed on Feb. 19, 2016.

(51) Int. Cl.
*C07C 29/60* (2006.01)
*C07C 29/00* (2006.01)
(Continued)

(52) U.S. Cl.
CPC ............. *C07C 29/60* (2013.01); *B01J 21/066* (2013.01); *B01J 23/868* (2013.01); *B01J 23/892* (2013.01);
(Continued)

(58) Field of Classification Search
None
See application file for complete search history.

(56) References Cited

U.S. PATENT DOCUMENTS 3,691,100 A    9/1972   Wright
4,066,711 A * 1/1978   Melaja .................... C07C 29/74
                                                                         568/872

(Continued)

FOREIGN PATENT DOCUMENTS

CA      2344078 A1    3/2000
CA      2359337 A1    7/2000
(Continued)

OTHER PUBLICATIONS

International Search Report for International Application No. PCT/US2017/018260. International Filing Date Feb. 17, 2017, dated Apr. 20, 2017, 7 pages.
(Continued)

*Primary Examiner* — Rosalynd A Keys
(74) *Attorney, Agent, or Firm* — Cantor Colburn LLP

(57) ABSTRACT

Use of diverse biomass feedstock in a process for the recovery of target C5 and C6 alditols and target glycols via staged hydrogenation and hydrogenolysis processes is disclosed. Particular alditols of interest include, but are not limited to, xylitol and sorbitol. Various embodiments of the
(Continued)

present invention synergistically improve overall recovery of target alditols and/or glycols from a mixed C5/C6 sugar stream without needlessly driving total recovery of the individual target alditols and/or glycols. The result is a highly efficient, low complexity process having enhanced production flexibility, reduced waste and greater overall yield than conventional processes directed to alditol or glycol production.

19 Claims, 3 Drawing Sheets

(51) Int. Cl.
  *C07C 29/132* (2006.01)
  *C07C 29/141* (2006.01)
  *C07C 29/145* (2006.01)
  *C07C 29/149* (2006.01)
  *C07C 29/78* (2006.01)
  *C07C 31/20* (2006.01)
  *C07C 31/22* (2006.01)
  *C07C 31/26* (2006.01)
  *B01J 21/06* (2006.01)
  *B01J 23/86* (2006.01)
  *B01J 23/89* (2006.01)

(52) U.S. Cl.
  CPC ............ *C07C 29/00* (2013.01); *C07C 29/132* (2013.01); *C07C 29/141* (2013.01); *C07C 29/145* (2013.01); *C07C 29/149* (2013.01); *C07C 29/78* (2013.01); *C07C 31/202* (2013.01); *C07C 31/22* (2013.01); *C07C 31/26* (2013.01); *Y02P 20/52* (2015.11)

(56) References Cited

U.S. PATENT DOCUMENTS

| | | |
|---|---|---|
| 5,081,026 A | 1/1992 | Heikklla et al. |
| 5,096,820 A | 3/1992 | Leleu et al. |
| 5,139,795 A | 8/1992 | Duross |
| 5,144,024 A | 9/1992 | Pepper et al. |
| 5,162,517 A | 11/1992 | Darsow |
| 5,238,826 A | 8/1993 | Leleu et al. |
| 5,340,403 A | 8/1994 | Fields et al. |
| 5,563,303 A | 10/1996 | Vuorinen |
| 5,631,150 A | 5/1997 | Harkki et al. |
| 5,641,872 A | 6/1997 | Darsow |
| 5,686,277 A | 11/1997 | Kim et al. |
| 5,714,602 A | 2/1998 | Beck et al. |
| 5,728,225 A | 3/1998 | Duflot et al. |
| 5,731,467 A | 3/1998 | Fleche |
| 5,739,303 A | 4/1998 | Beck et al. |
| 5,773,604 A | 6/1998 | Lefevre et al. |
| 5,846,794 A | 12/1998 | Delobeau et al. |
| 5,866,382 A | 2/1999 | Hallborn et al. |
| 5,936,081 A | 8/1999 | Degelmann et al. |
| 5,951,777 A | 9/1999 | Nurmi et al. |
| 5,980,640 A | 11/1999 | Nurmi et al. |
| 5,998,181 A | 12/1999 | Kim et al. |
| 5,998,607 A | 12/1999 | Heikkila et al. |
| 6,057,438 A | 5/2000 | Hyatt et al. |
| 6,103,894 A | 8/2000 | Degelmann et al. |
| 6,110,323 A | 8/2000 | Marsland |
| 6,124,443 A | 9/2000 | Darsow |
| 6,177,598 B1 | 1/2001 | Brunner et al. |
| 6,221,634 B1 | 4/2001 | Takeuchi et al. |
| 6,224,776 B1 | 5/2001 | Heikkila et al. |
| 6,239,274 B1 | 5/2001 | Heikkila et al. |
| 6,242,228 B1 | 6/2001 | Sugiyama et al. |
| 6,262,307 B1 | 7/2001 | Freund et al. |
| 6,262,318 B1 | 7/2001 | Heikkila et al. |
| 6,271,007 B1 | 8/2001 | Apajalahti et al. |
| 6,297,409 B1 | 10/2001 | Choque et al. |
| 6,303,353 B1 | 10/2001 | Sugiyama et al. |
| 6,340,582 B1 | 1/2002 | Suzuki et al. |
| 6,417,346 B1 | 7/2002 | Salome et al. |
| 6,441,255 B1 | 8/2002 | Haas et al. |
| 6,451,123 B1 | 9/2002 | Saska et al. |
| 6,458,570 B1 | 10/2002 | Elseviers et al. |
| 6,486,366 B1 | 11/2002 | Ostgard et al. |
| 6,498,248 B1 | 12/2002 | Cunningham et al. |
| 6,512,110 B1 | 1/2003 | Heikkila et al. |
| 6,538,133 B1 | 3/2003 | Aoki et al. |
| 6,570,043 B2 | 5/2003 | Elliott et al. |
| 6,572,775 B2 | 6/2003 | Heikkila et al. |
| 6,663,780 B2 | 12/2003 | Heikkila et al. |
| 6,723,540 B1 | 4/2004 | Harkki et al. |
| 6,752,902 B2 | 6/2004 | Heikkila et al. |
| 6,764,706 B1 | 7/2004 | Heikkila et al. |
| 6,846,657 B2 | 1/2005 | Heikkila et al. |
| 6,872,316 B2 | 3/2005 | Heikkila et al. |
| 6,875,349 B2 | 4/2005 | Heikkila et al. |
| 6,893,849 B2 | 5/2005 | Raj et al. |
| 6,894,199 B2 | 5/2005 | Heikkila et al. |
| 6,896,810 B2 | 5/2005 | Ali et al. |
| 6,896,811 B2 | 5/2005 | Heikkila et al. |
| 6,911,565 B2 | 6/2005 | Heikkila et al. |
| 6,982,328 B2 | 1/2006 | Werpy et al. |
| 6,995,107 B2 | 2/2006 | Shimazu et al. |
| 7,008,485 B2 | 3/2006 | Heikkila et al. |
| 7,022,824 B2 | 4/2006 | Vanoppen et al. |
| 7,060,188 B2 | 6/2006 | Paananen et al. |
| 7,109,005 B2 | 9/2006 | Eroma et al. |
| 7,141,666 B2 | 11/2006 | Van Lancker |
| 7,226,761 B2 | 6/2007 | Miasnikov et al. |
| 7,229,558 B2 | 6/2007 | Heikkila et al. |
| 7,238,242 B2 | 7/2007 | Pinatti et al. |
| 7,247,458 B2 | 7/2007 | Bao et al. |
| 7,271,244 B2 | 9/2007 | Dotson et al. |
| 7,314,528 B2 | 1/2008 | Koivikko et al. |
| 7,361,273 B2 | 4/2008 | Heikkila et al. |
| 7,407,586 B2 | 8/2008 | Jumppanen et al. |
| 7,482,144 B2 | 1/2009 | Ojamo et al. |
| 7,527,951 B2 | 5/2009 | Londesborough et al. |
| 7,598,374 B2 | 10/2009 | Bemiller et al. |
| 7,618,917 B2 | 11/2009 | Vanoppen et al. |
| 7,625,728 B2 | 12/2009 | Eroma et al. |
| 7,652,131 B2 | 1/2010 | Werpy et al. |
| 7,678,950 B2 | 3/2010 | Yao et al. |
| 7,699,958 B2 | 4/2010 | Griffith et al. |
| 7,713,418 B2 | 5/2010 | Frank et al. |
| 7,745,177 B2 | 6/2010 | Kim et al. |
| 7,771,983 B2 | 8/2010 | Spodsberg et al. |
| 7,781,191 B2 | 10/2010 | Dunson, Jr. et al. |
| 7,807,419 B2 | 10/2010 | Hennessey et al. |
| 7,812,153 B2 | 10/2010 | Svenson et al. |
| 7,820,414 B2 | 10/2010 | Kim et al. |
| 7,846,702 B2 | 12/2010 | Oh et al. |
| 7,932,063 B2 | 4/2011 | Dunson, Jr. et al. |
| 7,943,350 B2 | 5/2011 | Vlasenko et al. |
| 7,959,811 B2 | 6/2011 | Airaksinen et al. |
| 7,960,152 B2 | 6/2011 | Taylor et al. |
| 7,968,704 B2 | 6/2011 | Hirth et al. |
| 7,985,847 B2 | 6/2011 | Belanger et al. |
| 7,977,083 B1 | 7/2011 | Sakakibara et al. |
| 7,982,059 B2 | 7/2011 | Liu et al. |
| 7,993,884 B2 | 8/2011 | Jordan et al. |
| 8,044,264 B2 | 10/2011 | Lopez De Leon et al. |
| 8,058,513 B2 | 11/2011 | Brown et al. |
| 8,063,267 B2 | 11/2011 | Harris et al. |
| 8,080,128 B2 | 12/2011 | Chen et al. |
| 8,080,386 B2 | 12/2011 | Harris et al. |
| 8,114,638 B2 | 2/2012 | Zhao et al. |
| 8,124,394 B2 | 2/2012 | Maiyuran et al. |
| 8,129,591 B2 | 3/2012 | Brown et al. |
| 8,143,021 B2 | 3/2012 | Duan et al. |
| 8,148,103 B2 | 4/2012 | Tang et al. |
| 8,148,495 B2 | 4/2012 | Harris et al. |
| 8,158,778 B2 | 4/2012 | Komiya |
| 8,192,968 B2 | 6/2012 | Edwards et al. |
| 8,216,809 B2 | 7/2012 | Diner et al. |

(56) References Cited

U.S. PATENT DOCUMENTS

| | | |
|---|---|---|
| 8,222,463 B2 | 7/2012 | Kalnes et al. |
| 8,236,542 B2 | 8/2012 | Cascao-Pereira et al. |
| 8,258,370 B2 | 9/2012 | Harris et al. |
| 8,268,121 B2 | 9/2012 | Blount |
| 8,273,181 B2 | 9/2012 | Foody et al. |
| 8,278,070 B2 | 10/2012 | Diner et al. |
| 8,278,078 B2 | 10/2012 | Huang et al. |
| 8,283,139 B2 | 10/2012 | Park et al. |
| 8,287,652 B2 | 10/2012 | Heikkila et al. |
| 8,288,615 B2 | 10/2012 | Lassen et al. |
| 8,298,796 B2 | 10/2012 | Tolan et al. |
| 8,304,213 B2 | 11/2012 | Diner et al. |
| 8,309,694 B2 | 11/2012 | Belanger et al. |
| 8,323,944 B2 | 12/2012 | Harris et al. |
| 8,328,947 B2 | 12/2012 | Anand et al. |
| 8,337,663 B2 | 12/2012 | Xu et al. |
| 8,343,736 B2 | 1/2013 | Kim et al. |
| 8,377,668 B2 | 2/2013 | Medoff et al. |
| 8,389,253 B2 | 3/2013 | Diner et al. |
| 8,409,835 B2 | 4/2013 | Huang et al. |
| 8,420,356 B2 | 4/2013 | Medoff et al. |
| 8,426,158 B2 | 4/2013 | Xu et al. |
| 8,445,236 B2 | 5/2013 | Hennessey et al. |
| 8,445,704 B2 | 5/2013 | O'Connor et al. |
| 8,455,233 B2 | 6/2013 | Harris et al. |
| 8,460,898 B2 | 6/2013 | Diner et al. |
| 8,497,105 B2 | 7/2013 | Walther et al. |
| 8,524,471 B2 | 9/2013 | Koltermann et al. |
| 8,524,474 B2 | 9/2013 | Sabesan et al. |
| 8,541,651 B2 | 9/2013 | Wogulis |
| 8,551,250 B2 | 10/2013 | Vente et al. |
| 8,552,230 B2 | 10/2013 | Yao et al. |
| 8,563,277 B1 | 10/2013 | Parekh et al. |
| 8,569,581 B2 | 10/2013 | Maiyuran et al. |
| 8,575,426 B2 | 11/2013 | Harris et al. |
| 8,580,536 B2 | 11/2013 | McBrayer et al. |
| 8,581,042 B2 | 11/2013 | Morant et al. |
| 8,586,346 B2 | 11/2013 | Liu et al. |
| 8,586,827 B2 | 11/2013 | Tang et al. |
| 8,586,828 B2 | 11/2013 | Krogh et al. |
| 8,586,829 B2 | 11/2013 | Duan et al. |
| 8,597,917 B2 | 12/2013 | Medoff et al. |
| 8,603,788 B2 | 12/2013 | Donaldson et al. |
| 8,604,277 B2 | 12/2013 | Schnorr et al. |
| 8,900,841 B2 | 12/2014 | Medoff et al. |
| 8,936,929 B2 | 1/2015 | Donaldson et al. |
| 9,090,579 B2 | 7/2015 | Binder et al. |
| 9,102,951 B2 | 8/2015 | Griffin et al. |
| 9,187,741 B2 | 11/2015 | Spodsberg |
| 9,260,367 B2 | 2/2016 | Goldberg et al. |
| 9,315,427 B2 | 4/2016 | Foody et al. |
| 9,328,359 B2 | 5/2016 | Sauer et al. |
| 9,371,551 B2 | 6/2016 | Xu |
| 9,394,556 B2 | 7/2016 | Borjesson et al. |
| 9,441,255 B2 | 7/2016 | Tian et al. |
| 9,434,972 B2 | 9/2016 | Gaspar et al. |
| 9,446,102 B2 | 9/2016 | Borjesson et al. |
| 9,447,539 B2 | 9/2016 | Zhang et al. |
| 9,476,036 B2 | 10/2016 | Shasky et al. |
| 9,493,850 B2 | 11/2016 | Van Lancker |
| 9,546,385 B2 | 1/2017 | Argyros et al. |
| 9,562,222 B2 | 2/2017 | Morant |
| 9,586,878 B2 | 3/2017 | Yi et al. |
| 9,598,669 B2 | 3/2017 | Argyros et al. |
| 9,624,481 B2 | 4/2017 | Liu et al. |
| 9,670,510 B2 | 6/2017 | Xu et al. |
| 9,676,830 B2 | 6/2017 | Wogulis et al. |
| 9,677,060 B2 | 6/2017 | Johansen et al. |
| 9,683,225 B2 | 6/2017 | Spodsberg et al. |
| 9,687,839 B2 | 6/2017 | Ma |
| 9,689,011 B2 | 6/2017 | Ellegard et al. |
| 9,695,433 B2 | 7/2017 | Zhang et al. |
| 9,714,416 B2 | 7/2017 | Iyer et al. |
| 9,725,489 B2 | 8/2017 | Schnorr et al. |
| 9,751,916 B2 | 9/2017 | Brown et al. |
| 9,771,568 B2 | 9/2017 | Liu et al. |
| 9,783,861 B2 | 10/2017 | Jansen et al. |
| 9,790,530 B2 | 10/2017 | Shaghasi et al. |
| 9,609,834 B1 | 11/2017 | Li et al. |
| 9,840,621 B2 | 12/2017 | South et al. |
| 9,885,029 B2 | 2/2018 | Spodsberg |
| 9,926,547 B2 | 3/2018 | Spodsberg et al. |
| 9,963,727 B2 | 5/2018 | Medoff et al. |
| 9,963,730 B2 | 5/2018 | Medoff et al. |
| 9,969,994 B2 | 5/2018 | Liu et al. |
| 9,970,015 B2 | 5/2018 | Shasky et al. |
| 9,994,832 B2 | 6/2018 | Schnorr et al. |
| 10,036,050 B2 | 7/2018 | Wogulis |
| 10,227,579 B2 | 3/2019 | Lin et al. |
| 10,308,921 B2 | 6/2019 | Tang et al. |
| 2002/0061561 A1 | 5/2002 | Mihara et al. |
| 2003/0105301 A1 | 6/2003 | Li et al. |
| 2003/0148482 A1 | 8/2003 | Takenaka et al. |
| 2004/0143024 A1 | 7/2004 | Yoshino et al. |
| 2005/0065336 A1 | 3/2005 | Karstens |
| 2005/0148055 A1 | 7/2005 | Walther et al. |
| 2006/0009661 A1 | 1/2006 | Arndt et al. |
| 2006/0110811 A1 | 5/2006 | Kim |
| 2006/0281913 A1 | 12/2006 | Ferreira et al. |
| 2007/0072280 A1 | 3/2007 | Cirino et al. |
| 2008/0038784 A1 | 2/2008 | D'Arnaud-Taylor |
| 2008/0230051 A1 | 9/2008 | Bonke |
| 2008/0293109 A1 | 11/2008 | Berka et al. |
| 2009/0053800 A1 | 2/2009 | Friend et al. |
| 2009/0076260 A1 | 3/2009 | Kuusisto et al. |
| 2009/0123979 A1 | 5/2009 | Xu |
| 2009/0130707 A1 | 5/2009 | Xu |
| 2009/0270609 A1 | 10/2009 | Heikkila et al. |
| 2010/0031399 A1 | 2/2010 | Maranta et al. |
| 2010/0129860 A1 | 5/2010 | McFarland et al. |
| 2010/0159515 A1 | 6/2010 | Cirakovic |
| 2010/0159522 A1 | 6/2010 | Cirakovic |
| 2010/0159536 A1 | 6/2010 | Sweeney et al. |
| 2010/0170504 A1 | 7/2010 | Zhang |
| 2010/0268000 A1 | 10/2010 | Parekh et al. |
| 2010/0291645 A1 | 11/2010 | Zhao et al. |
| 2010/0297704 A1 | 11/2010 | Li |
| 2010/0304437 A1 | 12/2010 | Garner et al. |
| 2010/0306881 A1 | 12/2010 | Harris et al. |
| 2011/0003356 A1 | 1/2011 | Jain et al. |
| 2011/0009614 A1 | 1/2011 | Blommel et al. |
| 2011/0039320 A1 | 2/2011 | Li et al. |
| 2011/0061135 A1 | 3/2011 | Krogh et al. |
| 2011/0072540 A1 | 3/2011 | Brown et al. |
| 2011/0094505 A1 | 4/2011 | Bulla et al. |
| 2011/0117612 A1 | 5/2011 | Yukawa et al. |
| 2011/0152514 A1 | 6/2011 | Kettling et al. |
| 2011/0160482 A1 | 6/2011 | Nagaki et al. |
| 2011/0183382 A1 | 7/2011 | Schmalisch et al. |
| 2011/0201061 A1 | 8/2011 | Johal et al. |
| 2011/0207190 A1 | 8/2011 | Subramanian et al. |
| 2011/0207192 A1 | 8/2011 | Pigeau et al. |
| 2011/0212495 A1 | 9/2011 | Diner |
| 2011/0230682 A1 | 9/2011 | Schmalisch et al. |
| 2011/0245491 A1 | 10/2011 | Airaksinen et al. |
| 2011/0250645 A1 | 10/2011 | Schiffino et al. |
| 2011/0250646 A1 | 10/2011 | Bazzana et al. |
| 2011/0269188 A1 | 11/2011 | Bohan et al. |
| 2011/0269201 A1 | 11/2011 | Gray et al. |
| 2011/0296558 A1 | 12/2011 | Lopez De Leon et al. |
| 2011/0318796 A1 | 12/2011 | Walther |
| 2012/0005788 A1 | 1/2012 | Richard et al. |
| 2012/0009631 A1 | 1/2012 | Yang et al. |
| 2012/0021467 A1 | 1/2012 | Zhang et al. |
| 2012/0058526 A1 | 3/2012 | Jansen et al. |
| 2012/0064346 A1 | 3/2012 | Kataoka et al. |
| 2012/0064592 A1 | 3/2012 | O'Mullan et al. |
| 2012/0070864 A1 | 3/2012 | Liu et al. |
| 2012/0102823 A1 | 5/2012 | Hennessey et al. |
| 2012/0107689 A1 | 5/2012 | Doty et al. |
| 2012/0107888 A1 | 5/2012 | Schmalisch et al. |
| 2012/0122162 A1 | 5/2012 | Romero et al. |
| 2012/0192860 A1 | 6/2012 | Dhepe et al. |
| 2012/0172588 A1 | 7/2012 | Qiao et al. |

(56) References Cited

U.S. PATENT DOCUMENTS

| | | |
|---|---|---|
| 2012/0178976 A1 | 7/2012 | Hennessey et al. |
| 2012/0190092 A1 | 7/2012 | Jaquess et al. |
| 2012/0208235 A1 | 8/2012 | Zhang et al. |
| 2012/0231514 A1 | 9/2012 | Geertman et al. |
| 2012/0258503 A1 | 10/2012 | Raab et al. |
| 2012/0260371 A1 | 10/2012 | Brown et al. |
| 2012/0264873 A1 | 10/2012 | Eyal et al. |
| 2012/0272410 A1 | 10/2012 | Vlasenko et al. |
| 2012/0278952 A1 | 11/2012 | Vlasenko et al. |
| 2012/0280175 A1 | 11/2012 | Kania et al. |
| 2012/0282656 A1 | 11/2012 | Gibbs |
| 2012/0282660 A1 | 11/2012 | Van Groenestijn et al. |
| 2012/0289692 A1 | 11/2012 | Gray et al. |
| 2012/0325203 A1 | 12/2012 | Griffin et al. |
| 2012/0331587 A1 | 12/2012 | Lassen et al. |
| 2013/0011686 A1 | 1/2013 | Tolan et al. |
| 2013/0012610 A1* | 1/2013 | Belanger ............. C13K 13/00 521/177 |
| 2013/0018183 A1 | 1/2013 | Chang et al. |
| 2013/0029406 A1 | 1/2013 | Dottori et al. |
| 2013/0045509 A1 | 2/2013 | Romero |
| 2013/0052682 A1 | 2/2013 | Medoff et al. |
| 2013/0052687 A1 | 2/2013 | Medoff et al. |
| 2013/0065270 A1 | 3/2013 | Bell et al. |
| 2013/0071903 A1 | 3/2013 | Rowland et al. |
| 2013/0078677 A1 | 3/2013 | Fackler et al. |
| 2013/0078698 A1 | 3/2013 | Lali et al. |
| 2013/0079509 A1 | 3/2013 | Mattila et al. |
| 2013/0040346 A1 | 4/2013 | Wogulis |
| 2013/0115654 A1 | 5/2013 | Peterson et al. |
| 2013/0116424 A1 | 5/2013 | Peterson et al. |
| 2013/0117892 A1 | 5/2013 | Harris et al. |
| 2013/0130325 A1 | 5/2013 | Morant |
| 2013/0130326 A1 | 5/2013 | Morant |
| 2013/0130327 A1 | 5/2013 | Morant |
| 2013/0143277 A1 | 6/2013 | Gutierrez et al. |
| 2013/0143285 A1 | 6/2013 | Tolan et al. |
| 2013/0149758 A1 | 6/2013 | Medoff et al. |
| 2013/0164804 A1 | 6/2013 | Walther et al. |
| 2013/0203127 A1 | 6/2013 | Quinlan et al. |
| 2013/0180013 A1 | 7/2013 | Spodsberg |
| 2013/0183713 A1 | 7/2013 | Morant |
| 2013/0183729 A1 | 7/2013 | Huang et al. |
| 2013/0189734 A1 | 7/2013 | Liu et al. |
| 2013/0196387 A1 | 8/2013 | Liu et al. |
| 2013/0196399 A1 | 8/2013 | Hahn-Hagerdal et al. |
| 2013/0198910 A1 | 8/2013 | Spodsberg |
| 2013/0210086 A1 | 8/2013 | Vaaje-Kolstad et al. |
| 2013/0210087 A1 | 8/2013 | Liu et al. |
| 2013/0212745 A1 | 8/2013 | Spodsberg |
| 2013/0212746 A1 | 8/2013 | Spodsberg et al. |
| 2013/0217070 A1 | 8/2013 | Zhao et al. |
| 2013/0217077 A1 | 8/2013 | Quinlan et al. |
| 2013/0217078 A1 | 8/2013 | Tang et al. |
| 2013/0217079 A1 | 8/2013 | Wogulis et al. |
| 2013/0219567 A1 | 8/2013 | Schnorr et al. |
| 2013/0219568 A1 | 8/2013 | Sweeney et al. |
| 2013/0227748 A1 | 8/2013 | Sweeney et al. |
| 2013/0236933 A1 | 9/2013 | Huang et al. |
| 2013/0244294 A1 | 9/2013 | Medoff et al. |
| 2013/0244295 A1 | 9/2013 | Van Zyl et al. |
| 2013/0245252 A1 | 9/2013 | Makkee et al. |
| 2013/0252293 A1 | 9/2013 | Chen et al. |
| 2013/0260423 A1 | 10/2013 | Knudsen et al. |
| 2013/0266556 A9 | 10/2013 | Medoff |
| 2013/0273601 A1 | 10/2013 | Wisselink et al. |
| 2013/0273611 A1 | 10/2013 | Steffens et al. |
| 2013/0280761 A1 | 10/2013 | Teller et al. |
| 2013/0281741 A1 | 10/2013 | Chambon et al. |
| 2013/0288296 A1 | 10/2013 | Quinlan et al. |
| 2013/0288300 A1 | 10/2013 | Zhang et al. |
| 2013/0288301 A1 | 10/2013 | Spodsberg et al. |
| 2013/0288312 A1 | 10/2013 | Yu et al. |
| 2013/0289302 A1 | 10/2013 | Cortright |
| 2013/0303742 A1 | 11/2013 | Sutterlin et al. |
| 2013/0309723 A1 | 11/2013 | Huang et al. |
| 2014/0080182 A1 | 3/2014 | Jones et al. |
| 2014/0093920 A1 | 4/2014 | Zhang et al. |
| 2014/0120594 A1 | 5/2014 | Foody et al. |
| 2014/0141471 A1 | 5/2014 | Xu et al. |
| 2014/0147895 A1 | 5/2014 | Gaspar et al. |
| 2014/0202452 A1 | 7/2014 | Jansen et al. |
| 2014/0234897 A1 | 8/2014 | Zhang et al. |
| 2014/0245498 A1 | 8/2014 | Tang et al. |
| 2014/0304859 A1 | 10/2014 | Liu et al. |
| 2014/0308705 A1 | 10/2014 | Morant et al. |
| 2014/0323746 A1 | 10/2014 | Van Den Bergh et al. |
| 2014/0329284 A1 | 11/2014 | Wogulis et al. |
| 2014/0336338 A1 | 11/2014 | Mattila et al. |
| 2014/0342408 A1 | 11/2014 | Zhang et al. |
| 2014/0342418 A1 | 11/2014 | Jin et al. |
| 2015/0017670 A1 | 1/2015 | Quinlan et al. |
| 2015/0152455 A1 | 6/2015 | Schnorr et al. |
| 2015/0329887 A1 | 11/2015 | Wang et al. |
| 2016/0068678 A1 | 3/2016 | Li et al. |
| 2016/0368842 A1 | 12/2016 | Bernardi et al. |

FOREIGN PATENT DOCUMENTS

| | | |
|---|---|---|
| CN | 1032322 C | 7/1996 |
| CN | 1184853 A | 6/1998 |
| CN | 1284586 A | 2/2001 |
| CN | 1067970 C | 7/2001 |
| CN | 1068048 C | 7/2001 |
| CN | 1446784 A | 10/2003 |
| CN | 1515578 A | 7/2004 |
| CN | 1205338 C | 6/2005 |
| CN | 1721424 A | 1/2006 |
| CN | 1726175 A | 1/2006 |
| CN | 1290812 C | 2/2006 |
| CN | 1824767 A | 8/2006 |
| CN | 1830585 A | 9/2006 |
| CN | 1850833 A | 10/2006 |
| CN | 1284755 C | 11/2006 |
| CN | 1288249 C | 12/2006 |
| CN | 1884569 A | 12/2006 |
| CN | 1903866 A | 1/2007 |
| CN | 1320122 C | 6/2007 |
| CN | 101028996 A | 9/2007 |
| CN | 101138413 A | 3/2008 |
| CN | 101182341 A | 5/2008 |
| CN | 101200407 A | 6/2008 |
| CN | 101245565 A | 8/2008 |
| CN | 101255448 A | 9/2008 |
| CN | 101285082 A | 10/2008 |
| CN | 101323838 A | 12/2008 |
| CN | 101323870 A | 12/2008 |
| CN | 101440109 A | 5/2009 |
| CN | 100497277 C | 6/2009 |
| CN | 101445523 A | 6/2009 |
| CN | 101480549 A | 7/2009 |
| CN | 201279455 Y | 7/2009 |
| CN | 101497903 A | 8/2009 |
| CN | 101497904 A | 8/2009 |
| CN | 101514530 A | 8/2009 |
| CN | 201295607 Y | 8/2009 |
| CN | 201296736 Y | 8/2009 |
| CN | 101538589 A | 9/2009 |
| CN | 100569946 C | 12/2009 |
| CN | 100572543 C | 12/2009 |
| CN | 201353456 Y | 12/2009 |
| CN | 201358219 Y | 12/2009 |
| CN | 201365496 Y | 12/2009 |
| CN | 201366252 Y | 12/2009 |
| CN | 101619327 A | 1/2010 |
| CN | 101628852 A | 1/2010 |
| CN | 101628853 A | 1/2010 |
| CN | 201375898 Y | 1/2010 |
| CN | 101643752 A | 2/2010 |
| CN | 101643795 A | 2/2010 |
| CN | 101649565 A | 2/2010 |
| CN | 101659681 A | 3/2010 |
| CN | 101665523 A | 3/2010 |
| CN | 101676399 A | 3/2010 |

(56) References Cited

FOREIGN PATENT DOCUMENTS

| | | |
|---|---|---|
| CN | 101676403 A | 3/2010 |
| CN | 101705215 A | 5/2010 |
| CN | 101705253 A | 5/2010 |
| CN | 101705266 A | 5/2010 |
| CN | 101709309 A | 5/2010 |
| CN | 101717325 A | 6/2010 |
| CN | 101723799 A | 6/2010 |
| CN | 101747148 A | 6/2010 |
| CN | 101759525 A | 6/2010 |
| CN | 201493107 U | 6/2010 |
| CN | 101775413 A | 7/2010 |
| CN | 101747147 A | 8/2010 |
| CN | 101805701 A | 8/2010 |
| CN | 101805702 A | 8/2010 |
| CN | 101805703 A | 8/2010 |
| CN | 101805761 A | 8/2010 |
| CN | 101810262 A | 8/2010 |
| CN | 101818216 A | 9/2010 |
| CN | 101823939 A | 9/2010 |
| CN | 101829574 A | 9/2010 |
| CN | 101837973 A | 9/2010 |
| CN | 101838181 A | 9/2010 |
| CN | 101851150 A | 10/2010 |
| CN | 101851650 A | 10/2010 |
| CN | 101857523 A | 10/2010 |
| CN | 101857886 A | 10/2010 |
| CN | 101863737 A | 10/2010 |
| CN | 101870961 A | 10/2010 |
| CN | 101879424 A | 11/2010 |
| CN | 101899479 A | 12/2010 |
| CN | 101904484 A | 12/2010 |
| CN | 101914590 A | 12/2010 |
| CN | 101914592 A | 12/2010 |
| CN | 101921810 A | 12/2010 |
| CN | 102086145 A | 6/2011 |
| CN | 102093185 A | 6/2011 |
| CN | 102127236 A | 7/2011 |
| CN | 102134069 A | 7/2011 |
| CN | 102134616 A | 7/2011 |
| CN | 102154378 A | 8/2011 |
| CN | 201930724 U | 8/2011 |
| CN | 102220254 A | 10/2011 |
| CN | 102241707 A | 11/2011 |
| CN | 102250820 A | 11/2011 |
| CN | 102268490 A | 12/2011 |
| CN | 102391071 A | 3/2012 |
| CN | 102441346 A | 5/2012 |
| CN | 102452898 A | 5/2012 |
| CN | 102603504 A | 7/2012 |
| CN | 102634463 A | 8/2012 |
| CN | 102644210 A | 8/2012 |
| CN | 102660655 A | 9/2012 |
| CN | 102731252 A | 10/2012 |
| CN | 102731259 A | 10/2012 |
| CN | 102731581 A | 10/2012 |
| CN | 102758028 A | 10/2012 |
| CN | 102776244 A | 11/2012 |
| CN | 102794180 A | 11/2012 |
| CN | 102796797 A | 11/2012 |
| CN | 102838451 A | 12/2012 |
| CN | 102839198 A | 12/2012 |
| CN | 102936576 A | 2/2013 |
| CN | 102943050 A | 2/2013 |
| CN | 202725134 U | 2/2013 |
| CN | 102976895 A | 3/2013 |
| CN | 102994574 A | 3/2013 |
| CN | 102994575 A | 3/2013 |
| CN | 103012065 A | 4/2013 |
| CN | 103014093 A | 4/2013 |
| CN | 103015244 A | 4/2013 |
| CN | 103060217 A | 4/2013 |
| CN | 103130609 A | 6/2013 |
| CN | 103159587 A | 6/2013 |
| CN | 103184164 A | 7/2013 |
| CN | 103184165 A | 7/2013 |
| CN | 103184243 A | 7/2013 |
| DE | 1066567 B | 10/1959 |
| EP | 0432015 B1 | 10/1994 |
| EP | 0999197 A2 | 5/2000 |
| EP | 1065276 A1 | 1/2001 |
| EP | 0907627 B1 | 9/2001 |
| EP | 1176131 A1 | 1/2002 |
| FI | 101879 B | 9/1998 |
| GB | 2091254 A | 7/1982 |
| GB | 2095231 A | 9/1982 |
| GB | 2382038 A | 5/2003 |
| JP | 04197192 A | 6/1992 |
| WO | 9423931 A1 | 10/1994 |
| WO | 9731951 A1 | 9/1997 |
| WO | 0112834 A1 | 2/2001 |
| WO | 02088154 A1 | 11/2002 |
| WO | 02090601 A2 | 11/2002 |
| WO | 2006092432 A2 | 9/2006 |
| WO | 2006093364 A1 | 9/2006 |
| WO | 2008057263 A2 | 5/2008 |
| WO | 2008077640 A1 | 7/2008 |
| WO | 2010009515 A1 | 1/2010 |
| WO | 2010034055 A1 | 4/2010 |
| WO | 2010106052 A1 | 9/2010 |
| WO | 2010106055 A1 | 9/2010 |
| WO | 2011002824 A1 | 1/2011 |
| WO | 2011050424 A1 | 5/2011 |
| WO | 2011072264 A2 | 6/2011 |
| WO | 2011088422 A2 | 7/2011 |
| WO | 2011107760 A2 | 9/2011 |
| WO | 2011133984 A2 | 10/2011 |
| WO | 2011149956 A2 | 12/2011 |
| WO | 2012059643 A1 | 5/2012 |
| WO | 2012068310 A2 | 5/2012 |
| WO | 2012068537 A2 | 5/2012 |
| WO | 2012083244 A3 | 6/2012 |
| WO | 2012110231 A1 | 8/2012 |
| WO | 2012141523 A2 | 10/2012 |
| WO | 2013011205 A1 | 1/2013 |
| WO | 2013011206 A1 | 1/2013 |
| WO | 2013011207 A1 | 1/2013 |
| WO | 2013019822 A1 | 2/2013 |
| WO | 2013041298 A1 | 3/2013 |
| WO | 2013044859 A1 | 4/2013 |
| WO | 2013045318 A1 | 4/2013 |
| WO | 2013060293 A1 | 5/2013 |
| WO | 2013067964 A1 | 5/2013 |
| WO | 2013071871 A1 | 5/2013 |
| WO | 2013071883 A1 | 5/2013 |
| WO | 2013087027 A1 | 6/2013 |
| WO | 2013106113 A2 | 7/2013 |
| WO | 2013110242 A1 | 8/2013 |
| WO | 2013131225 A1 | 9/2013 |
| WO | 2013163230 A3 | 10/2013 |
| WO | 2013178919 A1 | 12/2013 |
| WO | 2013178920 A1 | 12/2013 |
| WO | 2014209664 A1 | 12/2014 |
| WO | 2015128202 A1 | 9/2015 |

OTHER PUBLICATIONS

Lazaridis, Polykarpos A.; "D-Glucose hydrogenation/hydrogenolysis reactions on noble metal (Ru, Pt)/activated carbon supported catalysts"; vol. 257, pp. 281-290. 2015.

Lee, Jechan et al.; "High-throughput screening of monometallic catalysts for aqueous-phase hydrogenation of biomass-derived oxygenates"; Applied Catalysis B: Environmental, vol. 140-141, pp. 98-107. 2013.

Li, Yuping et al.; "Advances in hexitol and thylene glycol production by one-pot hydrolytic hydrogenation and hydrogenolysis of cellulose"; Biomass and Bioenergy, vol. 74, pp. 148-161. 2015.

Liu, Chengwei et al.; "Aqueous-phase hydrogenolysis of glucose to value-added chemicals and biofuels: A comparative study of active metals"; Biomass and Bioenergy, vol. 72, pp. 189-199. 2015.

Sun, Jiying and Liu, Haichao; "Selective hydrogenolysis of biomass-derived xylitol to ethylene glycol and propylene glycol on Ni/C and basic oxide-promoted Ni/C catalysts"; Catalysis Today, vol. 234, pp. 75-82. 2014.

(56) References Cited

OTHER PUBLICATIONS

Written Opinion for International Application No. PCT/US2017018260. International Filing Date Feb. 17, 2017, dated Apr. 20, 2017.

Wu, Zhijie; "Selective conversion of cellulose into bulk chemicals over Bronsted acid-promoted ruthenium catalyst: one-pot vs. sequential process"; Green Chemistry, vol. 14, pp. 3336-3343, 2012.

Tajvidi et al. "Hydrogenolysis of Cellulose over Cu-Based Catalysts—Analysis of the Reaction Network," ChemSusChem 2014, 7, 1311-1317.

* cited by examiner

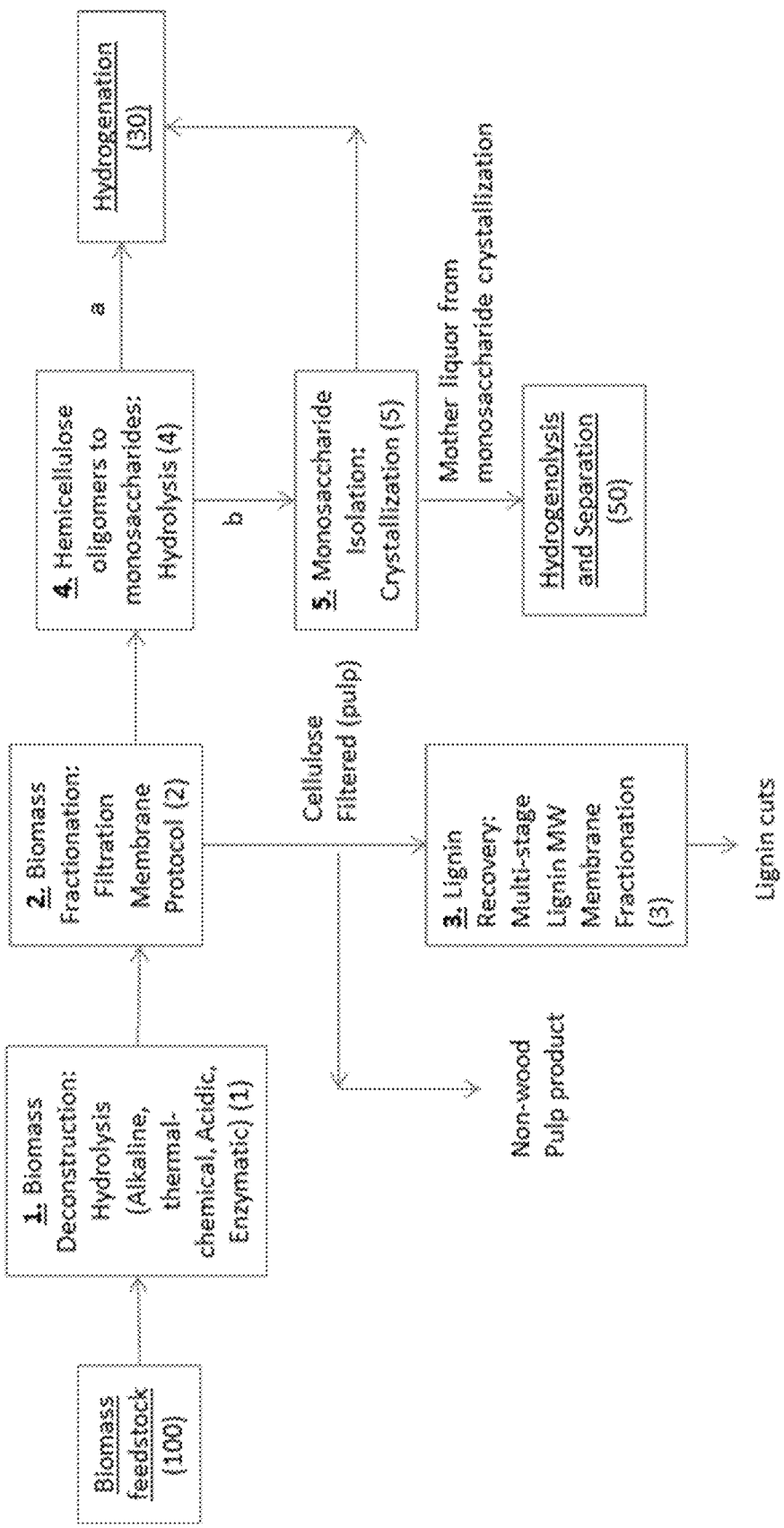

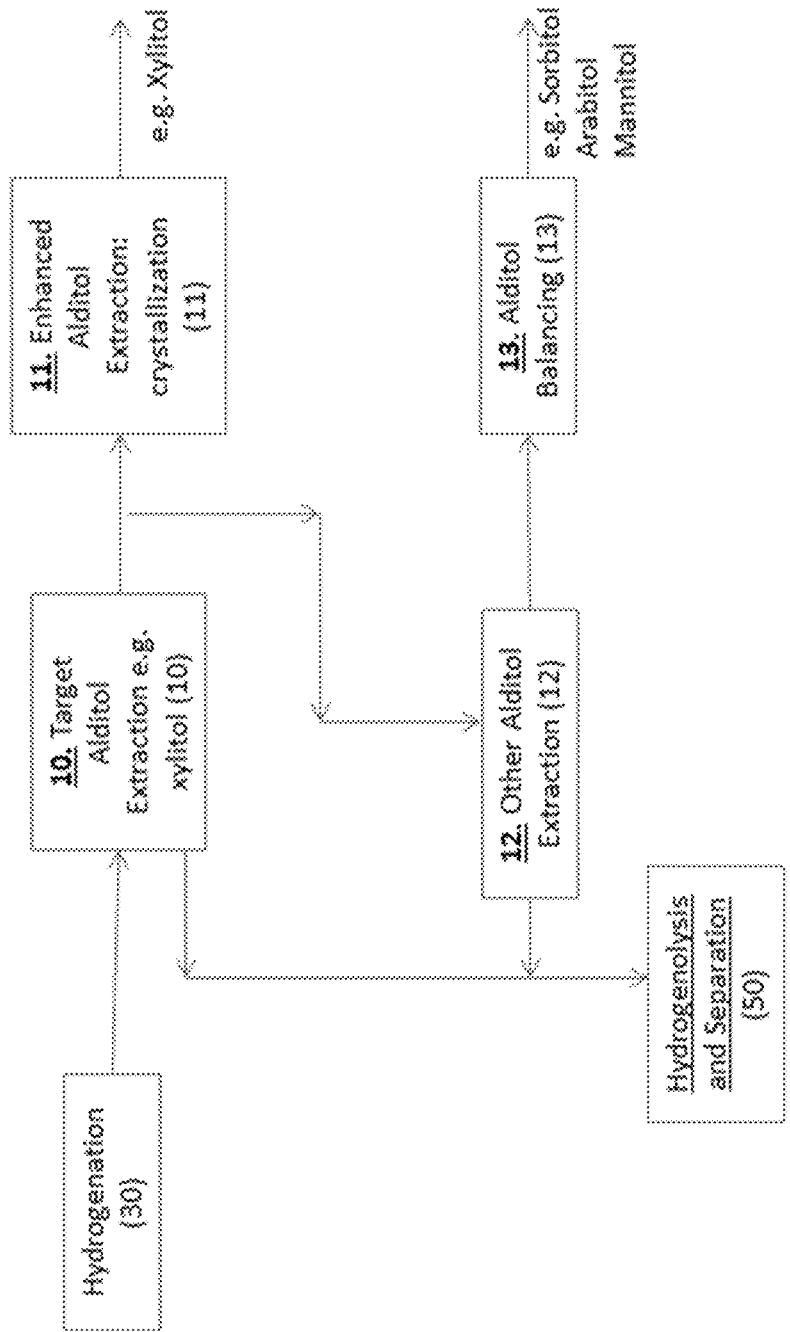

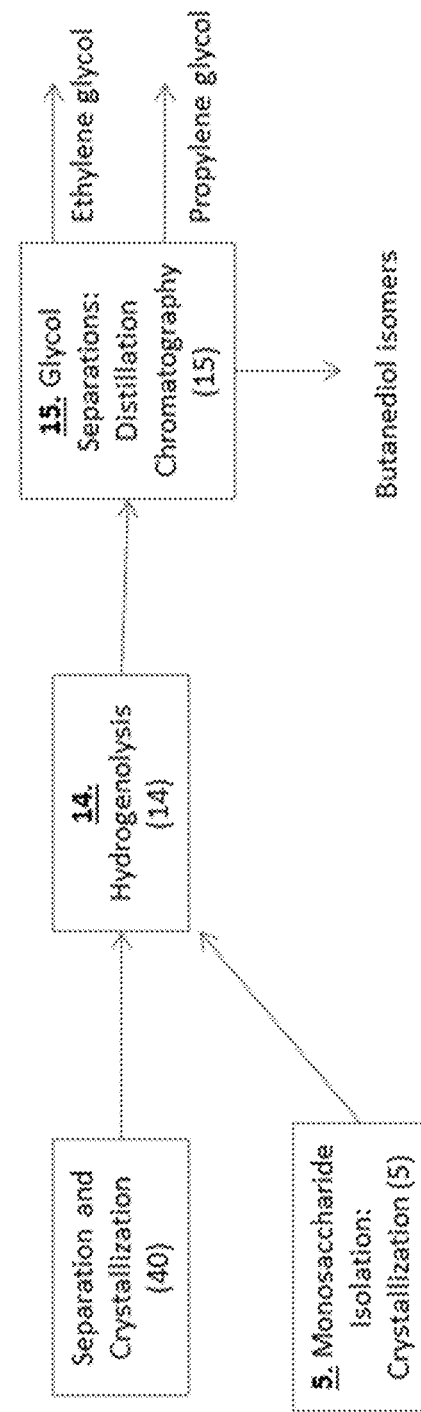

_US 10,759,727 B2_

PROCESSES TO CREATE MULTIPLE VALUE STREAMS FROM BIOMASS SOURCES

CROSS REFERENCE TO RELATED APPLICATIONS

This application is a National Stage application of PCT/US17/18260, filed Feb. 17, 2017, which claims the benefit of U.S. Provisional Application No. 62/297,434, filed Feb. 19, 2016, both of which are incorporated by reference in their entirety herein.

BACKGROUND

Processing of biomass-derived hemicellulose hydrolysates for the production of specific alditols is complicated, inefficient and costly. There are, for example, great difficulties in attaining a significant high purity alditol extraction yield through the use of hemicellulosic raw material feedstock. There are continually cascading losses associated with the various purification and separation unit operations, among other process steps, carried out in accordance with the established state-of-the-art, that result in hindered efficiency and reduced scale of alditol recovery. Currently, sorbitol is made from single stream C6 sugars, usually hydrogenated corn glucose, while xylitol is made from single stream C5 sugars derived from larch or poplar trees. There remains a need in the art for a process that can utilize mixed C5/C6 sugar streams derived from diverse unsegregated hemicellulosic feedstock to recover respective targeted C5/C6 alditols in addition to, and if desired, C2-C4 targeted glycols.

Indeed, there remains a need in the art for an efficient and high yielding process directed to the recovery of high purity alditols, and other target co-products, derived from diverse biomass while minimizing inefficiencies and losses associated with further downstream operations.

SUMMARY

In an embodiment, a process comprises optimizing an overall recovery of products without driving maximum individual recovery of each product, wherein the products comprise a target alditol or target blend of alditols, and a target glycol or target blend of glycols. The process includes hydrogenating a mixed C5/C6 monomer sugar stream to form a mixed C5/C6 alditol stream; isolating a target alditol or target blend of alditols, from the mixed C5/C6 alditol stream to leave a residual mixed C5/C6 alditol stream; hydrogenolysis of the residual mixed C5/C6 alditol stream to form a mixed C2-C4 glycol stream; and isolating a target glycol or target blend of glycols from the mixed C2-C4 glycol stream; wherein at least 10% of the overall target product yield is either target alditol/target blend of alditols or target glycol/target blend of glycols.

In another embodiment, a process comprises optimizing an overall recovery of products without driving maximum individual recovery of each product, wherein the products comprise xylitol, and a target glycol or target blend of glycols, the process comprising: hydrogenating a mixed C5/C6 monomer sugar stream to form a mixed C5/C6 alditol stream; isolating xylitol from the mixed C5/C6 alditol stream to leave a residual mixed C5/C6 alditol stream; hydrogenolysis of the residual mixed C5/C6 alditol stream to form a mixed C2-C4 glycol stream; and isolating a target glycol or target blend of glycols from the mixed C2-C4 glycol stream; wherein at least 10% of the overall target product yield is either xylitol or target glycol or target blend of glycols.

In yet another embodiment, a process comprises synergistically improving the overall recovery of products without the need to drive individual total recovery of each product, wherein the products comprise a target C5/C6 monomer sugar or target blend of C5/C6 monomer sugars, and a target glycol or target blend of glycols, the process comprising isolating a target C5/C6 monomer sugar or target blend of C5/C6 monomer sugars from a mixed C5/C6 monomer sugar stream to form a residual mixed C5/C6 monomer sugar stream; hydrogenolysis of the residual mixed C5/C6 monomer sugar stream to form a mixed C2-C4 glycol stream; and isolating a target glycol or target blend of glycols from the mixed C2-C4 glycol stream; wherein at least 10% of the overall target product yield is either target C5/C6 monomer sugar/target blend of C5/C6 monomer sugars or target glycol/target blend of glycols.

In another embodiment, a process comprises hydrogenating a monomer sugar stream to form a mixed alditol stream; recovering a target alditol or target blend of alditols from the mixed alditol stream to leave a residual mixed alditol stream; and hydrogenolysis of the residual mixed alditol stream to form a mixed C2-C4 glycol stream.

In another embodiment, a process comprises hydrogenating a monomer sugar stream to form a mixed alditol stream; recovering a target alditol or target blend of alditols from the mixed alditol stream to leave a residual mixed alditol stream; hydrogenolysis of the residual mixed alditol stream to form a mixed C2-C4 glycol stream; and recovering a target glycol or target blend of glycols from the mixed C2-C4 glycol stream.

In another embodiment, a process comprises hydrogenating a mixed C5/C6 monomer sugar stream to form a mixed C5/C6 alditol stream; recovering a target alditol or target blend of alditols from the mixed C5/C6 alditol stream to leave a residual mixed C5/C6 alditol stream; and hydrogenolysis of the residual mixed C5/C6 alditol stream to form a mixed C2-C4 glycol stream.

In another embodiment, a process comprises hydrogenating a mixed C5/C6 monomer sugar stream to form a mixed C5/C6 alditol stream; recovering a target alditol or target blend of alditols from the mixed C5/C6 alditol stream to leave a residual mixed C5/C6 alditol stream; hydrogenolysis of the residual mixed C5/C6 alditol stream to form a mixed C2-C4 glycol stream; and recovering a target glycol or target blend of glycols from the mixed C2-C4 glycol stream.

In another embodiment, a process comprises recovering at least one target monomer sugar from a mixed monomer sugar stream to leave a residual mixed monomer sugar stream; hydrogenating the recovered target monomer sugar to form at least one target alditol; hydrogenating at least a portion of the residual mixed monomer sugar stream to form a mixed alditol stream; and hydrogenolysis of the mixed alditol stream to form a mixed C2-C4 glycol stream.

In another embodiment, a process comprises selecting a target alditol or a target blend of alditols, hydrogenating continuously a mixed C5/C6 monomer sugar stream to form a mixed C5/C6 alditol stream; isolating the target alditol or target blend of alditols from the mixed C5/C6 alditol stream to leave a residual mixed C5/C6 alditol stream; continuous hydrogenolysis of the residual mixed C5/C6 alditol stream to form a mixed C2-C4 glycol stream; and isolating a target glycol or target blend of glycols from the mixed C2-C4 glycol stream; wherein at least 10% of the overall target product yield is either target alditol/target blend of alditols or target glycol/target blend of glycols.

As used herein the term "alditol" will be synonymous with "polyhydric alcohol", "sugar polyol", and "sugar alcohol". "Arabitol", "arabinol", "arabinitol", and "lyxitol" are synonymous. Exemplary alditols produced by the disclosed processes include xylitol, sorbitol, and the like. Exemplary five carbon (C5) alditols include arabitol, ribitol, and xylitol. Exemplary six carbon (C6) alditols include allitol, galactitol, iditol, mannitol, sorbitol, and talitol. "C5/C6 alditols" includes a mixture of alditols having any ratio of C5 to C6 alditols. "C5/C6 sugar monomer" means a mixture of monomer sugars (i.e. monosaccharides) having any ratio of a five carbon (C5) monosaccharide (pentose) to a six carbon (C6) monosaccharide (hexose). Exemplary C5 and C6 monosaccharides include those derived from plant biomass, specifically arabinose, lyxose, ribose, ribulose, xylose, and xylulose and C6 sugars such as fructose and glucose.

"Glycol" means a molecule having two hydroxyl (OH) groups attached to different carbon atoms. "Two carbon (C2), three carbon (C3), and four carbon (C4) glycols include ethylene glycol, propylene glycol, and butanediol isomers, respectively.

As used herein the terms "comprising" (also "comprises," etc.), "having," and "including" is inclusive (open-ended) and does not exclude additional, unrecited elements or method steps. The singular forms "a," "an," and "the" include plural referents unless the context clearly dictates otherwise. The endpoints of all ranges directed to the same characteristic or component are independently combinable, and inclusive of the recited endpoint. The term "a combination thereof" is inclusive two or more components of the list. The term "homogeneous" refers to a uniform blend of the components. The terms "first," "second," and the like, "primary," "secondary," and the like, as used herein do not denote any order, quantity, or importance, but rather are used to distinguish one element from another. As used in the Tables, "N/A" means not applicable; "ND" means not detected; and "TR" means trace.

BRIEF DESCRIPTION OF THE DRAWINGS

The accompanying drawings incorporated in and forming a part of the specification include:

FIG. 1 is an exemplary process flowsheet for a Biomass Front End stage (20) including Biomass Deconstruction (1) from Biomass feedstock (100), Biomass Fractionation (2), Lignin Recovery (3), Hemicellulose Oligomers converted to monosaccharides (4), and optional Monosaccharide Isolation (5).

FIG. 2 is a process flowsheet for the Separation and Crystallization stage (40) including Target Alditol Extraction (10) from the Hydrogenation (30) feed, Enhanced Alditol Extraction (11), Other Alditol Extraction (12), and Alditol Balancing (13).

FIG. 3 is a process flowsheet for the Hydrogenolysis and Separation stage (50) including Hydrogenolysis (14) and Glycol Separations (15).

DETAILED DESCRIPTION

Disclosed herein are unexpectedly synergistic and beneficial processes directed to alditol and/or glycol recovery from diverse hemicellulose-bearing biomass. Conventional xylitol production is typically focused singly on xylitol recovery from a single stream feedstock wherein the recovery is complicated, expensive, inefficient and difficult to attain high purity due to high levels of non-xylose aldose organics such as lignin and ash. The majority of the entire world xylitol industry, for example, predominantly utilizes corn cobs or larch/poplar based xylose feedstock that require extensive purification processing to drive the hydrogenation operations to total xylitol recovery at substantial time, expense, and complexity. Similarly, a significant amount of global ethylene glycol and propylene glycol production solely utilizes fossil fuel feedstock such as oil or natural gas. Glycol production does not, currently make large-scale commercial use of non-fossil fuel feedstocks such as cellulose biomass. These traditional manufacturing processes do not allow for the agnostic use of diverse feedstock starting materials nor allow for the in-line recovery and conversion of hydrogenation co-products.

Contrary to the current state of the art, the disclosed inventive processes allow for the use of agnostic diverse unsegregated or segregated feed stocks. For example, the inventive processes may use a single unsegregated feedstock composed of wheat straw, hardwood and beets and still further, the processes may also use alternating single segragated feed stocks of either wheat straw, hardwood or beets depending on supply availability, pricing fluctuations or the like. The disclosed feedstock-neutral processes thus avoid reliance on exotic, supply-limited, expensive feed stock for inefficient conversion while further increasing efficiency by the recovery and conversion of hydrogenation co-products. Indeed, the herein disclosed embodiments turn away from the existing art in order to maximize overall yield and dramatically improve overall plant flexibility and operational efficiency. Current methods of, for example, xylose and/or xylitol production fixate on maximizing yield, and minimizing waste, from a given mass of feedstock, and may employ multiple recovery and operation loops—with ever decreasing efficiency and yield per operation—to drive production. Similarly, several processes directed to the production of glycols (from sugars, alditol, glycerol, or similar) also focus operations on maximizing glycol yield to minimize waste by utilizing continually cascading, continually inefficient, operation loops. The numerous disclosed processes herein take approaches taught away from the art by not individually maximizing either xylitol or glycol yield. Rather, the disclosed processes synergistically optimize total yield by first recovering an initial fraction of xylitol while allowing the remainder to be converted to glycol. Xylitol yield is therefore decreased as some xylitol that would be recovered by the existing art is converted to glycol. Glycol yield is also decreased as some xylitol that could have been converted into glycol is recovered as xylitol. The yield of either xylitol or glycol is seemingly suboptimal and greatly discouraged by the current art. Unexpectedly and synergistically, however, the embodiments of the disclosed processes actually promote increased total combined yield of both xylitol and glycol (rather than the individual and countervailing productions), therefore increasing plant efficiency. As described herein, the processes are not limited to the production of xylitol and glycol.

Thus, in this way, multiple product streams of interest—for example, xylitol and propylene glycol; sorbitol and ethylene glycol; or a mix of xylose/sorbitol and butanediols—can be recovered without the typical limitations of driving maximum yield of any individual target product component negatively impacting overall efficiency, cost, and waste generation.

In one general embodiment, the process comprises selecting at least two target products based on a feedstock source such that the overall product yield of the at least two target products is such that the process is more efficient than if one were to try and maximize the yield of only a single product. The feedstock source can be a biomass feedstock, a hydrolysate stream, a monomer sugar stream, or a combination thereof as discussed in more detail herein. In an embodiment, at least 90% of the feedstock source is converted to target alditols and glycols. In an embodiment, the feedstock source is converted into the at least two target products where at least 10% of the overall target product yield is one of the at least two target products, more specifically at least 15%, at least 20%, or at least 25% of the overall target product yield. If needed to maintain the overall target product yield, the process further comprises modifying the selection of the at least two target products if there is a change in the feedstock source. The at least two target products can be a target [C5/C6] alditol, a target blend of [C5/C6] alditols, a target [C5/C6] monomer sugar, a blend of target [C5/C6] monomer sugars, a target C2-C4 glycol, a target blend of C2-C4 glycols, an organic acid, a compound in Table A herein, or a combination thereof, and specifically wherein at least one of the target products is a target C2-C4 glycol or a target blend of C2-C4 glycols. Further within this embodiment, the number of operation loops or operational treatments is conducted no more than two or three times on any single feedstock stream, specifically no more than two times, and more specifically one time. The operation loop or operational treatment can be a hydrogenation, a hydrogenolysis, a biomass deconstruction process, or an isolation process as discussed herein. The feedstock stream can be any starting feedstock or intermediate feedstock stream created in the process. Exemplary feedstock streams include a biomass feedstock stream, a hydrolysate stream, a monomer sugar stream, an alditol stream, a glycol stream, or a combination thereof, as described herein. In a further embodiment, a feedstock stream can be modified or augmented with external material to change the feedstock stream composition.

More specifically, disclosed herein is an embodiment directed at the conditioning of C5 sugars from C5 containing monomer sugar streams that may be derived from a variety of biomass sources and converting those conditioned (purified) sugars into specific target alditols via hydrogenation and into specific target glycols via hydrogenolysis. The process may be directed to the production of target C5/C6 alditols and target C2-C4 glycols from biomass derived mixed C5/C6 sugar streams, overcoming the efficiency and total product yield challenges of the prior art. Alternatively, a process may be directed at conditioning a C5 monomer sugar stream whereby the C5 stream may contain 2-4 carbon sugars, 6-12 carbon sugars, glycerol, glycols, impurities or the like. Alternatively, a process is directed at the conditioning of mixed C5 and C6 sugars in varying C5/C6 ratios derived from various biomass sources and isolating a target monomer sugar (e.g., xylose) or a blend of target monomer sugars with the residual material converted into specific target glycols via hydrogenolysis. Such described processes, including any of the hydrogenation or hydrogenolysis, may be batch or continuous. In any number of embodiments, additional alditol may be provided to the hydrogenolysis of the residual mixed C5/C6 alditol stream to form a mixed C2-C4 glycol stream.

The generation of alditols and glycols as co-products is achieved by the combination of hydrogenation of hemicellulose based monomer C5/C6 hydrolysates to alditols with downstream hydrogenolysis of the residual materials after target alditol crystallization/removal to produce glycols. In short, after hydrogenation of aldoses to alditols and target alditol(s), many residual materials, including non-target alditols, may be converted into glycol products.

Suitable biomass feedstock should provide a mixture of monosaccharides that may, when hydrogenated, produce a variety of alditols. Accordingly, but without limitation, diverse sources such as wheat straw, bagasse, sulfite pulp liquor, hardwood, hybrid poplar, grasses, sugarcane, beets, starch, etc. may be used as feedstock for the inventive processes disclosed herein. After hydrolysis, the hydrolyzed solution provides a monomer sugar stream, the stream for example having at least one C5 sugar, at least one C6 sugar, or combinations thereof ("mixed monomer sugar stream"). The hydrolyzed mixed monomer sugar stream may be purified and is then hydrogenated to produce a mixed alditol stream, containing more than one alditol such as any combination of xylitol, mannitol, and sorbitol ("mixed alditol stream"). Target alditols, such as xylitol and/or sorbitol, may be recovered from solution by, for example, crystallization or chromatography. These target alditols may be recovered at high purities suitable for food applications. Hydrolyzed solution components not recovered by the alditol isolation step (the "residual mixed alditol stream") may then undergo further hydrogenolysis to recover industrial or food-grade glycols. Optionally, additional alditols can be recovered after, or before, target alditol crystallization if so desired, rather than being treated to produce glycol, according to the principle of "balanced overall total product or stoichiometric recovery and value".

The components from the hydrolysate stream obtained by the deconstruction and hydrolysis of the biomass feedstock material may be characterized chemically and/or physically determined. Determinations include: dry weight percentage of each component of the hydrolysate stream, ratio of C5 to C6 sugars in hydrolysate stream, ratio of xylose and/or arabinose to total C5 sugars in hydrolysate stream. From this information, the designed balance of recovery of target materials in their respective forms is determined through calculation to deliver an "optimal overall total product or stoichiometric recovery value". Many target alditols and target glycols can be made with this process. A method of calculating "optimal overall total product or stoichiometric recovery value" could be to account for the yield of target alditol against the yield of target glycol. For example, in an embodiment, xylitol is extracted from the main stream after the hydrolysate stream has undergone hydrogenation. After further processing, propylene glycol is purified from the stream. The ratio of xylitol yield to propylene glycol yield is measured and adjusted by modifying process parameters and conditions, biomass feedstocks, addition of other C5/C6 sources, etc. to arrive at an optimized overall total product yield (as compared to the individual and countervailing productions) or stoichiometric recovery value. The same may be practiced with arabitol as the target alditol and ethylene glycol as the target glycol, or any combination of any alditol as target alditol and any glycol as target glycol including blends or mixtures of glycols as target glycol and blends or mixtures of alditols. For example, a blend of xylitol and sorbitol could be made as target alditol and a blend of propylene glycol and ethylene glycol could be made as the target glycol.

Where xylitol is a target alditol, selection of composition and structure of biomass feedstocks suitable for the disclosed process may include a high ratio of xylose sugar derivatives compared to other sugar derivatives, and the ease of accessibility to extract the xylose sugar derivatives over the other components.

A high ratio of xylitol compared to other alditols, is exemplified by the xylitol having a concentration greater than or equal to 80% of the total alditol concentration. Thus, a solution concentrated to 80% w/w total sugar derived solids, with >80% of those solids being xylitol will have a net concentration of >=64% xylitol. A xylitol having a concentration greater or equal to 90% of the total alditol concentration provides a net concentration of 72%, which provides further higher yields. Where xylitol is the target alditol, the total C5 sugar content of the feedstock is specifically greater than 25%, specifically greater than 60%, and more specifically greater than 90%. In the same embodiment, the xylose content of the feedstock is specifically greater than 20%, more specifically greater than 50%, and even more specifically greater than 80%.

Suitable hydrogenation of aldoses, such as those in a mixed C5/C6 monomer sugar stream, may further include process steps that facilitate removal of ash, non-sugar organic compounds, and other inorganic species such as anion chlorides and phosphates. Biomass feedstock pretreatment and use of activated carbon may be used. Biomass feedstock may be converted to a useful C5 monomer sugar stream by deconstruction by a variety of thermo-mechanical, alkaline, enzymatic or acidic hydrogenation operations. The C5 monomer sugar stream may, optionally, contain 2-4 carbon sugars, 6-12 carbon sugars, glycerol, glycols, impurities or the like. A further optionally "clean" C5 stream may be further provided by subjecting a C5 stream to any number of downstream operations such as, by way of example but not limitation, fractionation, lignin recovery, monosaccharide isolation, and organic/inorganic impurity removal operations as shown in FIG. 1. In this way, among other benefits, catalyst operating life may be extended and impurities which inhibit alditol crystallization may be minimized.

To facilitate the crystallization of xylitol (as an exemplary target alditol product) can involve establishing and delivering threshold concentration levels of xylitol (minimum concentrations) and other alditols (maximum concentrations) to enable recovery of xylitol at efficient yield and with suitable purity for premium value applications. Further details are discussed in the Enhanced Alditol Extraction section below.

Crystallization of a target alditol product can also be facilitated by the optional use of an antisolvent (e.g., ethanol, or isopropanol) to increase alditol crystallization yield. Such antisolvent may also improve the ease of solid-liquid separation and filtration times.

In an embodiment, a process comprises purifying a mixed C5/C6 monomer sugar stream derived from a single biomass source to form a purified mixed C5/C6 monomer sugar stream, converting the purified mixed C5/C6 monomer sugar stream to C5/C6 alditols via hydrogenation; fractionating the C5/C6 alditols singly or purifying the C5/C6 alditols all or in part, and forming a residual mixed C5/C6 alditol stream (less targeted alditols). The residual mixed C5/C6 alditol stream (less targeted alditols) becomes a hydrogenolysis feedstock stream for glycols. Target alditol products can be removed as (solids) crystals or liquid concentrates.

In an embodiment, a process comprises purifying a mixed C5/C6 monomer sugar stream derived from a diverse biomass source and combining the purified mixture with C5/C6 monomer sugars (with for example significantly higher C5 levels) and adding these concentrated aldoses to existing C5/C6 monomer sugars sources to enhance target C5 or C6 aldoses and converting the purified mixed C5/C6 and/or augmented aldose sugar stream to C5/C6 alditols via hydrogenation; and fractionating the C5/C6 alditols singly or purifying the C5/C6 alditols all or in part. Also C5/C6 concentrated aldose streams could also be selectively hydrogenated to mixed alditols with targeted alditols removed by crystallization, etc and then external alditols (such as glycerin) added to the residual mixed C5/C6 alditol stream prior to hydrogenolysis. As used herein "glycerin" is the same as "glycerol".

In one embodiment, external C5 monomer rich streams (from any source) can be added to the mixed C5/C6 monomer sugar stream derived from a single or diverse biomass source to augment C5/C6 monomer sugar ratios prior to hydrogenation and then target alditol(s) extracted. Further external non-targeted alditols (such as C3 glycerin or C6 sorbitol) can be added after hydrogenation and target alditol removal to augment the downstream hydrogenolysis conversion to glycols.

The integrated process to produce target alditols and target glycols as co-products involves the unique combination of hydrogenation of hemicellulose hydrolysates to alditols (mother liquor) followed by target alditols removal from the mother liquor with downstream hydrogenolysis (of the residual materials after target alditol crystallization) to produce glycols. The residual materials from target alditol recovery include non-target alditols (e.g., mixtures in varying ratios of arabitol, xylitol, sorbitol, mannitol, etc.).

In a specific embodiment, a concentrated solution of monomer sugars is provided where the principle component is xylose, 70% or more of the solids present. If the total solids concentration of this solution is raised to 75%-80% solids, a significant proportion of the xylose present can then be separated by fractional crystallization from the solution. The crystalline xylose thus produced is separated from the mother liquor in a filter or centrifuge and then dried and packed in bags or drums. The xylose can then be converted to xylitol by dissolution in water, hydrogenation with, for example, a Raney Nickel catalyst and further crystallization.

A variety of biomass feedstock may be useful for the disclosed processes including, by way of example but without limitation, bagasse (e.g., sugarcane bagasse, sorghum bagasse, or sugarbeet pulp), corn cobs, corn husks, corn kernal pericarp, corn stover, grain straw (e.g., alfalfa, barley, oat, rice, or wheat), grasses (e.g., switch grass), hardwoods (e.g., birch, poplar, alder, eucalyptus, and the like), plant leaves, plant stalks, softwoods (e.g., cedar, hemlock, pine, or spruce), sulfite pulp liquor, xylans from algae polysaccharides, or combinations thereof In an embodiment of this process the biomass is not a genetically modified organism (GMO) or derived from a genetically modified species, i.e., the biomass is non-GMO or "GMO free". In a specific embodiment, the feedstock to obtain C5-rich sugar content (e.g., 60-80%) is non-GMO sugarcane bagasse, wheat straw, poplar, hybrid poplar, alder, or a combination thereof.

By way of example but not limitation, the following industrially useful compositions (singly and in combination) may be recovered from mixed C5/C6 monomer sugar streams by various embodiments disclosed herein are shown in Table A.

TABLE A

| | |
|---|---|
| Formic Acid | Arabinitol |
| Methanol | Furfural |
| Carbon Monoxide | Glutamic acid |
| Acetaldehyde | Glutaric acid |
| Acetic acid & anhydride | Itaconic acid |

TABLE A-continued

| | |
|---|---|
| Ethanol | Levulinic acid |
| Glycine | Proline |
| Oxalic acid | Xylitol |
| Ethylene glycol | Xylonic acid |
| Ethylene oxide | Aconitic acid |
| Alanine | Adipic acid |
| Glycerol | Ascorbic acid |
| 3-Hydroxypropionic acid | Citric acid |
| Lactic acid | Fructose |
| Malonic acid | 2,5 Furan dicarboxylic acid |
| Serine | Glucaric acid |
| Propionic acid | Gluconic acid |
| Acetone | Kojic & Comeric acid |
| Acetoin | Lysine |
| Aspartic acid | Sorbitol |
| Butanol | |
| Fumaric acid | |
| Hydroxybutryolactone | |
| Malic acid | |
| Succinic acid | |
| Threonine | |

Hydrogenation

A C5/C6 monomer sugar stream may be used directly as a hydrogenation feed where the hydrogenation process converts the monomers to alditols to result in a mixed C5/C6 alditol stream. Alternatively, the C5/C6 monomer sugar stream can be concentrated to increase the total solids content prior to hydrogenation. Such concentration processes are discussed herein. Still further, ethanol, methanol, isopropanol, n-propanol and the like can be used in the hydrogenation process as individual or mixtures of co-solvent(s). The hydrogenation process may be a batch process, continuous process or combinations thereof.

Exemplary hydrogenation catalysts include those hydrogenation catalysts suited to high pH (9 and above), high temperature, and aqueous conditions. Such catalysts include transition metal catalysts, such as nickel catalysts supported on zirconium, titanium, or other heavy metal oxide substrates; sponge metal nickel catalyst; or the like. In an embodiment, the catalyst comprises a combination of a zirconium compound and polyacid/promoter material, which forms a zirconyl-promoter precursor having a molar ratio between 2:1 and 20:1; and the polyacid/promoter material can be a polyacid comprising the oxide or acid form of chromium, molybdenum, tungsten, or a combination thereof. In another embodiment, the catalyst comprises nickel, a promoter selected from bismuth, silver, tin, antimony, gold, lead, thallium, cerium, lanthanum, manganese, or a combination thereof, and a support selected from zirconia or carbon. In an embodiment, the hydrogenating process is conducted using a nickel-based catalyst with a substrate of zirconium oxide, titanium dioxide, aluminum oxide, silicon oxide, chromium oxide or a combination thereof.

In an embodiment, the catalyst comprises a support comprising zirconium oxide promoted by a polyacid or promoter material, where the support is impregnated with a catalytically active metal such as Group 4 (Group IVA) metals, Group 10 (Group VIII) metals, Group 11 (Group IB) metals, or a combination thereof.

In an embodiment, the hydrogenation process involves a continuous down-flow trickle bed reactor involving a combined three phase of solid (hydrogenation catalyst), liquid (mixed C5/C6 monomer sugar stream of about 20 to about 30% w/w total solids content, specifically about 22% to about 25% w/w total solids content), and gas (hydrogen). The process further utilizes a hydrogen pressure of about 600 to about 2000 psig; a temperature of about 100 to about 160° C., specifically about 140 to about 160° C.; a residence time of about 20 to about 40 minutes; and a starting pH of about 9 to about 12, specifically about 10 to about 11, to achieve about 99% stoichiometric conversion of monomer sugars to alditols.

In an embodiment, the hydrogenation process comprises a feed stream of about 20% to about 25% monomer sugar in dry weight basis where the C5 sugars, xylose and arabinose, are present at about 80% and the C6 sugars glucose and fructose are present at about 20% levels; hydrogen gas at about 4 to about 6 times stoichiometric; a starting pH of about 8.0 to about 11.0, specifically about 9.0 to about 10.0; a temperature of about 120 to about 140° C.; a hydrogen pressure of about 1200 to about 2000 psig, specifically about 1800 psig; and a Liquid Hourly Space Velocity ("LHSV") of about 0.4 to 3.0, specifically about 1.0-1.5. In this embodiment, the hydrogenation catalyst may be a transition metal nickel-based (20-40% nickel) catalyst on a zirconium and/or titanium substrate support matrix or a Raney nickel based (20-60% nickel with copper promoter) in dissolved aluminum matrix catalyst formulated for fixed bed trickle reactor. Within the Raney nickel embodiment, an alkaline hydroxide promoter can be used, such as sodium hydroxide or potassium hydroxide to maintain pH in the 8.0 to 10.0 range.

The conversion of the C5/C6 monomer sugars to the corresponding C5/C6 alditols in the hydrogenation process is at least 95%, specifically at least 97% and more specifically about 100%.

An optional two-stage hydrogenation can be employed if the stoichiometric conversion is less than 95%. For example, an optional second stage continuous reactor can be used whereby a stage one reactor targets 90-95% conversion of monomer sugars to alditols and a stage two reactor completes the 95-100% conversion to alditols. A two-stage reactor may be operated at higher LHSV—Liquid Hourly Space Velocity.

Known hydrogenation equipment and techniques can be used to conduct the hydrogenation process. In an embodiment, the equipment is a continuous trickle fixed bed reactor having a cylindrical column length:diameter ratio of about 10:2, specifically a fixed bed trickle down co-current reactor where the hydrogen and liquid feed comes down and the liquid comes out of the bottom. The reactor can be fitted to allow backwash and regeneration in situ. Hydrogen pressure may be about 600 to about 2000 psig, specifically about 1800 psig to 2000 psig.

The hydrogenation feed stream or product feed stream can have a total solids content of about 20 to about 27% w/w, specifically about 22 to about 25% w/w. Additionally, the pH of the hydrogenation feed stream can be about can be about 8.0 to about 11.0, specifically about 9 to about 10. Sodium hydroxide may be used as a pH adjustment alkali employed, though other alkalis such as potassium calcium or lithium hydroxide/oxides may also be used.

If required to achieve the desired feed concentration for the hydrogenation reaction feed, the mixed C5/C6 monomer sugar stream can be concentrated to increase total solids content by removal of water. In an embodiment, the mixed C5/C6 monomer sugar stream can be concentrated using a membrane to allow the passage of water while the mixed C5/C6 monomer sugar stream sees a composition concentration increase. A suitable exemplary membrane can be a 40-5000 Dalton membrane.

In an embodiment, hydrogenation is conducted on a purified mixed C5/C6 sugar stream comprising about 20 to about 25% w/w total sugars in water, a pH of about 11, a Liquid Hourly Space Velocity (LHSV) of about 1.0, a hydrogen pressure of about 2000 psig, about 3 to about 6 times stoichiometric hydrogen, and a temperature of about 140° C., and has a 99% or more C5/C6 monomer sugar to alditol conversion.

In yet another embodiment, a mixed C5/C6 alditol stream from the hydrogenation process comprises about 65% C5 alditols and about 35% C6 alditols. Further, a mixed C5/C6 alditol stream comprises about 50% xylitol, 15% arabinatol, 25% sorbitol and about 10% mannitol. In another embodiment, a mixed C5/C6 alditol stream comprises at least 50% xylitol, less than or equal to 15% arabinatol, less than or equal to 25% sorbitol, and less than or equal to 10% mannitol.

In an embodiment, when the hydrogenating process moves below 90% conversion of C5/C6 monomer sugars to alditols, the process further comprises a regeneration cycle where a purified mixed C5/C6 monomer sugar feed stream is sent to a sacrificial reactor of partially deactivated nickel substrate catalyst prior to direct hydrogenation to reduce sulfur poisoning and reactor fouling followed by staged water, caustic, and ethanol washing of the catalyst to remove fouling agents followed by hydrogen drying and reduction activation. Fouling includes one, several or all of the following—saccharification (scorching), burning, carbonization and/or caramelization of sugars, sulfur poisoning, incapacitation of catalytic reaction sites by impurities or intermediates, and polymerization of sugars resulting in the hydrogenation catalyst becoming physically compromised and plugged.

In an embodiment, hydrogenation production occurs with catalyst life exceeding 4000 total hours and with a suitable run time of about 1000 to about 1800 hours before a catalyst regeneration is staged. Catalyst regeneration may last for about 16 to about 36 hours or specifically 24 hours.

In an embodiment, a purified mixed C5/C6 monomer sugar stream comprises C5/C6 monomer sugar, specifically about 25 to about 50% ethanol, and specifically about 25 to about 50% water. Ethanol and water in concert with pH and temperature enhances organic polymeric impurity solubility and hence reduces downtime.

In an embodiment a given C5/C6 monomer sugar feedstock prior to hydrogenation can be augmented by, for example, addition of a more highly concentrated aldose stream. For example, xylose can be crystallized or concentrated separately from other C5/C6 streams and the concentrated C5 fraction added to a base C5/C6 monomer sugar fraction shifting the levels of C5s higher such as xylose or arabinose. In this way, target aldoses can be concentrated to make desired mixes for hydrogenation and respective downstream alditol and glycol recovery. Generally, the higher the concentration of target alditol in the post hydrogenation stream the greater the yield of purified target alditol. If the concentration of target alditol in the post hydrogenation stream is too low, for example below 25% w/w, then very little or no target alditol can be extracted. The concentration of the target alditol in the post hydrogenation stream can be increased, for example, by addition of a feedstock high in the aldose that is converted to the target alditol during hydrogenation. The concentration of target alditol can be greater than 25%, specifically greater than 60%, and more specifically greater than 90% in the post hydrogenation stream.

FIG. 2 is an exemplary process flow sheet for the Separation and Crystallization stage (40) including Target Alditol Extraction (10), Enhanced Alditol Extraction (11), Other Alditol Extraction (12), and Alditol Balancing (13).

Target Alditol Extraction

The hydrogenation product feed stream, which can be a mixed C5/C6 alditol stream, is processed to isolate target alditols or target alditol mixtures. The products of the isolation can be individual alditols (e.g., sorbitol or xylitol) or alditol mixtures (e.g., defined sorbitol, xylitol ratios for confectionery or cough syrup mixes). For example, extraction of xylitol can be achieved from an aqueous mixture of mixed alditols (xylitol, sorbitol and possible alditol isomers arabitol and mannitol) via single pass or staged crystallization by sequential water removal (for example by evaporative concentration at elevated temperature) and subsequent lowering of temperature to induce crystallization. The C5/C6 alditol extraction can be adapted to various feed stocks with varying C5/C6 alditol ratios.

\Water, and co-solvents (e.g., ethanol) if used, can be removed by processes including multiple effect evaporation, vapor distillation, multiple vapor recompression evaporators, reverse osmosis, or a combination thereof.

In an embodiment, the water removal is conducted at a temperature of about 30 to about 120° C. under vacuum, specifically about 70 to about 110° C. under reduced pressure, and more specifically about 80 to about 100° C. under reduced pressure, for example less than 200 mbar, specifically about 100 to about 180 mbar, and more specifically about 140 to about 165 mbar.

The concentrated feed stream can have a total dissolved solids content of about 40% to about 90% w/w, specifically about 60% to about 85% w/w, and more specifically about 75 to about 85% w/w.

Enhanced Alditol Extraction

Specific alditols, such as xylitol, arabitol, or sorbitol, or alditol mixtures can be isolated from an aqueous mixture of mixed alditols (such as xylitol, sorbitol, arabitol, and mannitol) via Generally Recognized As Safe (GRAS) solvent precipitation or crystallization, industrial chromatography including simulated moving bed (SMB), or a combination thereof, specifically GRAS solvent precipitation or crystallization, to isolate the target alditol or target alditol mixture. Crystalline forms of the target alditol can be sized to specification while liquid formulations of the target alditol mixes also can be made to specifications.

Suitable solvents include lower alcohols (e.g., ethanol, isopropanol, etc.) and mixtures thereof with water. An exemplary GRAS solvent includes ethanol.

Prior to crystallization or precipitation, the alditol (e.g., xylitol) solution can be treated with activated carbon to remove impurities, which may interfere with the alditol crystallization. Suitable activated carbon includes activated powdered carbon, granular activated carbon, and the like, or a combination thereof. Other processes to remove crystallization inhibitors include one or more of the following optionally in combination with activated carbon treatment: ion exchange, membrane filtration, solvent extraction. Other conditioning steps include staged electrodialysis, strong acid ion exchange resin treatment, and calcium sulfate chemical precipitation, and optionally further comprising reclaiming spent inorganic material. A determination of whether or not the alditol solution or mixed C5/C6 alditol stream requires prior conditioning (purification) before crystallization, and to what degree, can be accomplished by a skilled artisan without undue experimentation. For example, analytical techniques known in the art can be used to determine type and amount of components in the alditol solution or mixed C5/C6 alditol stream so that the appropriate purification technique(s) can be employed.

The crystallization process can be conducted using a continuous or a batch process. Crystallization equipment and techniques known in the art can be used to conduct the crystallization of the target alditol. Suitable crystallization equipment and solid-liquid separation equipment includes tank crystallizers (horizontal, vertical, cooling crystallizers, evaporative crystallizers), centrifuges, and the like.

After a desirable solids weight is achieved during the crystallization process, the target alditol solids can be isolated using known techniques in the art such as filtration, centrifugation, a combination thereof, and the like. The solids can be washed, dried, sized, or a combination thereof.

The mother liquor from the crystallization process can be further processed for additional crops of target alditol or another alditol or used as a feedstock ("residual mixed C5/C6 alditol stream") for the production of glycols via hydrogenolysis.

In an embodiment, the crystallization of a concentrated aqueous feed comprising predominantly xylitol (e.g., >75% of the total alditols) and low levels of other alditols such as galactitol, lyxitol, and sorbitol can be conducted by cooling a concentrated aqueous feed having a total dissolved solids content of about 50 to about 85% w/w, specifically about 65 to about 85% w/w, and more specifically about 70 to about 85% w/w, from about 60 to about 100° C. to a temperature of about −10 to about 40° C., specifically about 20 to about 35° C., whereupon a seed of the target alditol can be optionally added.

An antisolvent, such as ethanol, isopropanol, or another GRAS solvent can be optionally added to the concentrated aqueous feed while maintaining the temperature below the flash point of the antisolvent, for example below about 40° C., specifically below about 35° C., for ethanol. Optionally, a seed of the target alditol can optionally be added to induce and/or promote crystallization.

The concentrated aqueous feed can be cooled to a target temperature below room temperature, specifically about −10 to about 20° C. and more specifically about −5 to about 5° C. After crystallization of the target alditol, a slurry having a solids content of about 15 to about 45%, specifically about 20 to about 40% solids can be fed to a devices for solids recovery, such as a centrifuge, to separate the solid from the mother liquor. By this exemplary method high purity (>98%) additol may be achieved, though cooling may be adjusted as per the desired yield versus solid product purity.

In an embodiment, the crystallization of xylitol as the target alditol in pure form from mixed alditol streams can involve establishing and delivering threshold concentration levels of xylitol (minimum concentrations) and other alditols (maximum concentrations) to enable recovery of xylitol at efficient yield and with suitable purity for premium value applications. The threshold levels are dependent upon the ratio of water:antisolvent present in the system.

The concentration of the component in the crystallization liquor is calculated as % total solids multiplied by the proportional concentration of the alditol of the total solids.

The threshold concentration may be affected by the following factors;
Solubility limit of the component in the solvent at the temperature used
Impact of antisolvent (and its concentration)
Impact on the solubility of the component by other solutes, which can either depress or enhance its solubility
The tendency of another component to interfere with crystallization of the desired crystalline component e.g. through being incorporated in the crystalline lattice of the desired component.

Examples of threshold limits have been determined to be in the following regions, i.e. maximum levels of each alditol in the crystallization liquor that still enable effective purification of xylitol, when xylitol is the target alditol:
In general, the presence of high concentrations of sorbitol and mannitol exhibit a significant effect on the physical behavior of the crystallization of xylitol. Such that high levels of sorbitol and mannitol result in co-crystallization of sorbitol and/or mannitol with the xylitol whereby the filtration speed of the resulting mixture may be inhibited.

For xylitol, at least 20% w/w, more specifically greater than about 42% w/w xylitol concentration based on the weight of total solids is required for xylitol to be produced, more specifically greater than 60% w/w in solution to deliver a better yield; (for example 80% of total solids in a solution with a minimum of 80% w/w xylitol of the total solids). Further within this xylitol embodiment, arabinitol concentration was less than 10% w/w of total solids otherwise the xylitol purification is impaired. Also within this xylitol embodiment, mannitol has a low solubility level thus a threshold level of 10% w/w concentration is set. At a level greater than 10% w/w mannitol based on total solids, undesirable co-crystallization of mannitol with xylitol is observed. In an embodiment the mannitol content of 4% w/w or less of the crystallization liquor was found to enable successful purification of xylitol. Further within this xylitol embodiment, when sorbitol is present at concentrations of greater than or equal to 15% w/w of total solids then the rate of crystallization and the filtration speeds are reduced.

Within this embodiment regarding xylitol threshold, xylitol represents a minimum of 60% of total solids, more specifically greater than 80% of total solids, and after evaporative concentration to a minimum of 75% w/w of total solids in solution at about 60 to about 70° C. the actual concentration of xylitol is specifically greater than 60%. If an antisolvent is used in this embodiment, the actual concentration of xylitol is greater than 50%. Maximum threshold levels of other components are dependent upon the ratio of water:antisolvent present in the system. Arabitol is present at less than 10% in a 50:50 water:ethanol system as greater concentrations of this alditol have a negative impact on the kinetics and purity of xylitol crystallization. Mannitol is present at less than 4% due to co-crystallization with xylitol. The exact threshold levels can vary slightly based on the overall composition of the liquor, and the amount of antisolvent.

The xylitol crystallization solution can have a total dissolved solids content high enough for controlled xylitol crystallization, but low enough to avoid rapid bulk crystallization. In several embodiments, the crystallization solution can have a total dissolved solids content of about 40% to about 80% w/w, specifically about 60% to about 85% w/w, and more specifically about 70 to about 75% w/w.

In an embodiment for xylitol crystallization, the xylitol content as % of total solids of the crystallization solution is 50% or more, specifically 55% or more, more specifically 60% or more. Further within this embodiment, the amount of arabitol as % of total solids of the crystallization solution is less than or equal to 10%, specifically less than or equal to 5%, and more specifically less than or equal to 2%. Alternatively within this embodiment, the amount of mannitol as % of total solids of the crystallization solution is less than or equal to 10%, specifically less than or equal to 5%, and more specifically less than or equal to 2%. Alternatively within this embodiment, the amount of arabitol as % of total solids of the crystallization solution is less than or equal to 10%, specifically less than or equal to 5%, and more specifically less than or equal to 2%; and the amount of mannitol as % of total solids of the crystallization solution is less than or equal to 10%, specifically less than or equal to 5%, and more specifically less than or equal to 2%. Within this embodiment, the solution does not include an antisolvent. In another embodiment, the solution can comprise a combination of water and an antisolvent such as ethanol, specifically about a 95:5 ratio of water:ethanol to a 5:95 ratio of water:ethanol, more specifically about a 95:5 ratio of water:ethanol to a 5:95 ratio of water:ethanol.

In an embodiment for xylitol crystallization, the xylitol content as % of total solids of the crystallization solution is 50% or more, specifically 55% or more, more specifically 60% or more; and the amount of sorbitol as % of total solids of the crystallization solution is less than or equal to 15%, specifically less than or equal to 10%, and more specifically less than or equal to 5%. Within this embodiment, the solution does not include an antisolvent. In another embodiment, the solution can comprise a combination of water and ethanol, specifically about a 95:5 ratio of water:ethanol, to a 0:1 ratio of water:ethanol.

In an alternative embodiment, chromatography may be used to separate the alditols, thus removing the need to control threshold levels at the alditol crystallization stage.

In an embodiment, a mixed C5/C6 alditol stream is as least partially separated by chromatography into a C5 alditol fraction and a C6 alditol fraction.

In an embodiment, a mixed C5/C6 alditol stream is separated by chromatography into a C5 alditol fraction and a C6 alditol fraction; and a target alditol is crystallized from the C5 alditol fraction using ethanol and water. The mother liquid containing the residual alditols can be directed to the hydrogenolysis process for conversion to glycols.

In an embodiment, isolating a target alditol from a mixed C5/C6 alditol stream via crystallization includes removing ethanol, water, or a combination thereof from the mixed C5/C6 alditol stream.

In an embodiment, a target alditol is a C5 alditol or a C6 alditol.

In an embodiment, a target alditol is xylitol. In an embodiment, a target alditol is sorbitol or arabitol.

In an embodiment, the xylitol obtained from the crystallization process contains about 90 to about 100% xylitol, specifically about 96 to about 99.99% xylitol and more specifically about 98.5 to about 99.99% xylitol. In an embodiment, the xylitol obtained from the crystallization process contains less than 1% other alditols.

Other Alditol Extraction

After the target alditol or alditol mixture has been extracted from the alditol stream, the remaining mixed alditol aqueous feed containing a fraction of the target alditol, such as xylitol, may be processed to fractionate sorbitol, arabitol, mannitol, or combinations thereof, via industrial chromatography. The target alditol products of this stage can be in either liquid or crystalline form. Optionally, a target alditol, typically about 85% to about 95% purity may be concentrated and crystallized in a second extraction.

Alditol Balancing

After extraction of a majority of target alditols (e.g., xylitol or sorbitol) from the alditol stream, the remaining C5/C6 alditol balance can be shifted to prepare remaining alditols for hydrogenolysis and hence specific glycol product slates. For example high C6 would tend to favor propylene glycol and butanediol isomers as hydrogenolysis products, while C5 alditols would favor ethylene glycol and glycerin as a hydrogenolysis product.

Processes such as chromatography, precipitation, and the like can produce separate fractions rich in C5 alditols and in C6 alditols. Conducting hydrogenolysis on the enriched fractions will lead to target glycol products.

FIG. 3 is a process flow sheet for the Hydrogenolysis and Separation stage (50) including Hydrogenolysis (14) and Glycol Separations (15).

Hydrogenolysis

Residual alditols and alditol mixtures can be converted via hydrogenolysis to target hydrogenolysis products including glycols and glycerin. The hydrogenolysis can be conducted at high temperature and pressure in the presence of hydrogen.

Exemplary target glycols to be formed include: ethylene glycol, propylene glycol, 1-3 propane diol, butanol, butanediol isomers (1,2 butanediol; 1,4 butanediol; 1,3 butanediol; and 2,3 butanediol), and mixtures thereof. Glycerin can be another target hydrogenolysis product.

Exemplary hydrogenolysis catalysts include transition metal, noble metal catalysts, metal catalysts on a support matrix formulated for aqueous conditions and high pH (above 9). Exemplary catalyst described above for the hydrogenation process can be used in the hydrogenolysis process. In one embodiment, the hydrogenolysis catalyst is a nickel-based (20-40% nickel) on a zirconia or titanium dioxide substrate support matrix.

In an embodiment, the hydrogenolysis is conducted at a temperature of about 240° C.; a pressure of about 1000 to about 2000 psig; a pH of about 10 or greater; and a Liquid Hourly Space Velocity (LHSV) of about 0.5 to about 3.0.

In an embodiment, the hydrogenolysis is conducted at a temperature of about 210 to about 250° C., specifically about 220 to about 240° C.; a pressure of about 1000 to about 2000 psig, specifically about 1200 to about 1800 psig; a pH of about 9.0 to about 11.0, specifically about 10.0; and a Liquid Hourly Space Velocity (LHSV) of about 0.5 to about 2.0, specifically about 0.8 to about 1.5, and more specifically about 1.0. Further within this embodiment, a feed of about 20 to about 25% mixed alditols (e.g., C5/C6 alditols) in water dry weight basis is used. The amount of hydrogen can be about 4 to about 6 times stoichiometric. Further within this embodiment, a promoter such as sodium hydroxide is used. The conversion of C5/C6 alditol to mixed glycols can be greater than 70%, specifically greater than 80%.

In an embodiment, the process comprises hydrogenolyzing continuously a residual mixed C5/C6 alditol stream having about 20 to about 25 w/w % total solids content of alditol in water, a pH of about 11, a LHSV of about 1.0, a hydrogen pressure of about 2000 psig, and a temperature of about 240° C. in the presence of a nickel based catalyst to form the mixed glycol stream comprising propylene glycol, ethylene glycol, glycerin, butanediol isomers, or a combination thereof.

In an embodiment, the hydrogenolysis process produces a mixed glycol stream comprising propylene glycol (about 15% to about 25%), ethylene glycol (about 20% to about 30%), glycerin (about 10% about 30%) and butanediol isomers (about 10% to about 20%).

The hydrogenolysis feed and the resulting mixed glycol stream of the hydrogenolysis process can comprise ethanol and water. Here ethanol can be added as a co-solvent enhancing hydrogen solubility and lowering energy requirements. Alcohols have a lower heat of vaporization and use of an ethanol/water low boiling azeotrope allows for a further reduction in energy costs.

In an embodiment, a residual mixed C5/C6 alditol stream used as a hydrogenolysis feed for the hydrogenolyzing process can comprise alditol, about 25 to about 50% ethanol, and about 25 to about 50% water.

In an embodiment, the hydrogenolyzing process is conducted using a nickel-based catalyst with a substrate including zirconium oxide, titanium dioxide, or a combination thereof.

In an embodiment, when the hydrogenolyzing process moves below 90% conversion of C5/C6 alditols to glycols, the process further comprises a regeneration cycle including staged hot water, caustic, and ethanol catalyst washing to remove fouling agents followed by hydrogen drying and reduction activation.

Glycol Separations

The product stream of the hydrogenolysis process containing a mixture of glycols and glycerin can be separated into target hydrogenolysis products including target glycol products. Exemplary separation processes include a combination of classical distillation, extractive processes, and extractive and/or azeotropic distillation to isolate and purify close boiling glycols. Target hydrogenolysis products include ethylene glycol, propylene glycol, glycerin and butanediol isomers.

Propylene glycol can be separated into industrial-grade and United States Pharmacopeia (USP)-grade propylene glycol via azeotropic distillation. Ethylene glycol can be separated into industrial-grade and polyethylene terephthalate ("PET") resin-grade ethylene glycol via azeotropic distillation. Butanediols can be concentrated and purified into individual 1,2; 2,3 and 1,3 butanediols respectively for industrial use. Glycerin can be extracted and or recycled into the mixed alditol hydrotreating feedstock prior to hydrogenolysis and converted to propylene glycol and ethylene glycol.

In an embodiment, a process to generate C5/C6 alditols and C2-C4 glycols from biomass-derived mixed C5/C6 sugar streams, comprises deconstructing and hydrolyzing a biomass source under alkaline, acidic, enzymatic, or acidic and enzymatic conditions to form a biomass hydrolysate stream comprising one or more of a sugar monomer, oligomeric sugar, hemicellulose, cellulose, solubilized lignin, and impurities such as non-sugar organic compounds, ash, and inorganic contaminants; conditioning the biomass hydrolysate stream to remove lignin, non-sugar organic compounds, and inorganic contaminants to form a purified mixed C5/C6 sugar stream; acid hydrolyzing the purified mixed C5/C6 sugar stream to form a mixed C5/C6 monomer sugar stream; hydrogenating the mixed C5/C6 monomer sugar stream to form a mixed C5/C6 alditol stream; isolating a target alditol from the mixed C5/C6 alditol stream via crystallization to leave a residual mixed C5/C6 alditol stream; hydrogenolysis the residual mixed C5/C6 alditol stream to form a mixed glycol stream; and isolating a target glycol. Within this embodiment, the deconstructing and hydrolyzing a biomass source is conducted under alkaline conditions. Within this embodiment, the biomass is derived from wheat straw. Within this embodiment, the conditioning is conducted using select progressive membranes and carbon treatment. Within this embodiment, the hydrogenation is conducted under nickel fixed bed catalysis; and the hydrogenolysis is conducted under nickel catalyst. In an embodiment, the target alditol is xylitol and the target glycol is propylene glycol. The inorganic contaminants removed are chlorides, sulfates, phosphates, or a combination thereof.

The xylitol, sorbitol, other alditols, and certain alditol mixtures (e.g., defined sorbitol, xylitol ratios) prepared by the disclosed processes can be used in a wide variety of applications including use as a sweetener in foodstuff and oral care products, as a component in pharmaceuticals, and for industrial applications. As a sweetener, it can be used alone or in combination with other sweeteners in confectionery, chewing gum, sauces, beverages, and the like. As xylitol is non-cariogenic and does not affect insulin levels of people with diabetes, it finds particular use in foodstuff. In addition, because of its very high negative heat of solution, consumption of xylitol produces a cooling sensation in the mouth of the consumer. Because of this effect, xylitol is commonly used in chewing gum to provide a refreshing feeling. In pharmaceuticals it can be used as a sweetener, an excipient, and the like. Oral care products may include toothpaste, tooth powder, mouthwash, breath films, and the like.

The alditols also find use in various industrial applications including the preparation of resins and surfactants, use as a plasticizer for a variety of polymers, and the like.

The target glycols prepared by the disclosed processes include propylene glycol for widespread use industrially and for cosmetic and food applications; ethylene glycol target for resin grade quality for polyethylene terephthalate (PET) containers, and butanediol isomers for value-added pharmaceutical precursors and resins.

The pulp from the biomass deconstruction processes can be used to produce fiberboard, specialty paper and/or other pulp applications replacing conventional hardwood and softwood pulps.

Isolated lignin fractions can be used for specific industrial use including ligno-sulfonates, production of resins, and the like, or use as a low sulfur fuel.

In an embodiment, a process comprises, deconstructing poplar, bagasse, or a combination thereof using acidic conditions to form a mixed C5/C6 sugar stream; selecting a target alditol or a target blend of alditols; conditioning the mixed C5/C6 sugar stream to remove lignin, organic impurities and inorganic impurities; hydrolyzing the mixed C5/C6 sugar stream to form a mixed C5/C6 monomer sugar stream; hydrogenating continuously a mixed C5/C6 monomer sugar stream to form a mixed C5/C6 alditol stream; isolating the target alditol or target blend of alditols from the mixed C5/C6 alditol stream to leave a residual mixed C5/C6 alditol stream; continuous hydrogenolysis of the residual mixed C5/C6 alditol stream to form a mixed C2-C4 glycol stream; and isolating a target glycol or target blend of glycols from the mixed C2-C4 glycol stream; wherein at least 10% of the overall target product yield is either target alditol/target blend of alditols or target glycol/target blend of glycols; wherein the target alditol is xylitol and the target glycol is propylene glycol, or a combination thereof; and wherein xylitol isolated by crystallization optionally with ethanol or isopropanol antisolvent.

In another embodiment, a process comprises hydrogenating continuously a mixed C5/C6 monomer sugar stream to form a mixed C5/C6 alditol stream; isolating xylitol from the mixed C5/C6 alditol stream to leave a residual mixed C5/C6 alditol stream; continuous hydrogenolysis of the residual mixed C5/C6 alditol stream to form a mixed C2-C4 glycol stream; and isolating a target glycol or target blend of glycols from the mixed C2-C4 glycol stream; wherein at least 10% of the overall target product yield is either xylitol or target glycol or target blend of glycols.

In an embodiment, a process comprises isolating a target C5/C6 monomer sugar or target blend of C5/C6 monomer sugars from a mixed C5/C6 monomer sugar stream to form a residual mixed C5/C6 monomer sugar stream; continuous hydrogenolysis of the residual mixed C5/C6 monomer sugar stream to form a mixed C2-C4 glycol stream; and isolating a target glycol or target blend of glycols from the mixed C2-C4 glycol stream; wherein at least 10% of the overall target product yield is either target C5/C6 monomer sugar/target blend of C5/C6 monomer sugars or target glycol/target blend of glycols. Within this embodiment, the target C5/C6 monomer sugar can be xylose.

In another embodiment, a process comprises selecting at least two target products based on a source of biomass feedstock; converting the biomass feedstock into the at least two target products where at least 10% of the overall target product yield is one of the at least two target products; and if needed to maintain the overall target product yield, modifying the selection of the at least two target products if there is a change in the source of biomass feedstock; wherein one of the at least two target products is a target C2-C4 glycol or a target blend of C2-C4 glycols; and wherein the remainder of the at least two target products is a target [C5/C6] alditol, a target blend of [C5/C6] alditols, a target [C5/C6] monomer sugar, a blend of target [C5/C6] monomer sugars, or a combination thereof; and wherein an operational treatment is conducted no more than two or three times on any single feedstock stream, where the operational treatment is a hydrogenation, a hydrogenolysis, a biomass deconstruction process, or an isolation process; and the feedstock stream is a biomass feedstock stream, a hydrolysate stream, a monomer sugar stream, an alditol stream, a glycol stream, or a combination thereof. Within this embodiment, at least one step in the process can be conducted in a continuous manner. Further within this embodiment, the process can be conducted at a single production site or a single production line.

In an embodiment, a process comprises selecting at least two target products based on a source of a hydrolysate stream; converting the hydrolysate stream into the at least two target products where at least 10% of the overall target product yield is one of the at least two target products; and if needed to maintain the overall target product yield, modifying the selection of the at least two target products if there is a change in the source of the hydrolysate stream; wherein one of the at least two target products is a target C2-C4 glycol or a target blend of C2-C4 glycols; and wherein the remainder of the at least two target products is a target [C5/C6] alditol, a target blend of [C5/C6] alditols, a target [C5/C6] monomer sugar, a blend of target [C5/C6] monomer sugars, or a combination thereof; and wherein an operational treatment is conducted no more than two or three times on any single feedstock stream, where the operational treatment is a hydrogenation, a hydrogenolysis, or an isolation process; and the feedstock stream is the hydrolysate stream, a monomer sugar stream, an alditol stream, a glycol stream, or a combination thereof. Within this embodiment, at least one step in the process can be conducted in a continuous manner. Further within this embodiment, the process can be conducted at a single production site or a single production line.

In another embodiment, a process comprises selecting at least two target products based on a source of a mixed monomer sugar stream; converting the mixed monomer sugar stream into the at least two target products where at least 10% of the overall target product yield is one of the at least two target products; and if needed to maintain the overall target product yield, modifying the selection of the at least two target products if there is a change in the source of the mixed monomer sugar stream; wherein one of the at least two target products is a target C2-C4 glycol or a target blend of C2-C4 glycols; and wherein the remainder of the at least two target products is a target [C5/C6] alditol, a target blend of [C5/C6] alditols, a target [C5/C6] monomer sugar, a blend of target [C5/C6] monomer sugars, or a combination thereof and wherein an operational treatment is conducted no more than two or three times on any single feedstock stream, where the operational treatment is a hydrogenation, a hydrogenolysis, or an isolation process; and the feedstock stream is the monomer sugar stream, an alditol stream, a glycol stream, or a combination thereof. Within this embodiment, at least one step in the process can be conducted in a continuous manner. Further within this embodiment, the process can be conducted at a single production site or a single production line.

The features and advantages are more fully shown by the following examples, which are provided for purposes of illustration, and are not to be construed as limiting the invention in any way.

EXAMPLES

Example 1

Cellulose and small fractions of suspended lignin that are not dissolved in the alkaline pulp liquor and high molecular weight hemicellulose can be extracted with the cellulose to increase pulp yield. Pulping operating conditions can reduce hemicellulose molecular weight favoring higher hemicellulose recovery in the liquor and hence higher net C5/C6 sugars. Wheat straw hemicellulose has a typical xylan:glucan ratio of approximately 75:25 Therefore if all cellulose is removed (C6) then the highest C5 (xylose/arabinose) sugar yield possible would be 75% xylose/arabinose entirely from the hemicellulose fraction. If all wheat straw cellulose were converted to C6 sugars and in this case of wheat straw hemicellulose were converted to C5 and C6 sugars, there is a maximum 2.19 times as much C6 as C5 sugars. If all sugars (cellulose and hemicellulose) were converted to monomers, C5 would be a maximum of approximately 31% of total cellulose and hemicellulose sugars. If all C6 cellulose is removed the maximum C5 concentration of sugars from the hemicellulose fraction only would be 75%. Thus, it is possible to be able to target specific C5 to C6 sugars and ratios and to address corresponding pulp conditions and other pretreatments to favor a) specific sugars and sugars for hydrotreating and b) adjust C5 levels via C6 (cellulose) pulp recovery.

Example 2. Hydrogenation of C5/C6 Sugars

Xylose and arabinose (C5 sugars) and co-feedstock hexose C6 sugars (glucose, galactose, mannose and fructose) are hydrogenated at a dry weight sugar to water concentration of 20-25% at a pH of 10-12 at 125-150° C. and at 1800-2000 psig over a series of proprietary catalysts. Liquid hourly space velocity (LHSV) is 0.4-1.5 with a stoichiometric surplus of hydrogen of 4-6. Overall conversion is 99% of sugars to alditols. By-products include un-reacted aldoses and possible alternative C5 or C6 alditol isomers. Tables 2-A, 2-B, and 2-C summarize a series of hydrogenations with varying conditions and catalysts illustrating alditol production conditions.

Co-production of C5 and C6 alditols with target alditols being fractionated out and purified into industrial and/or food grade materials and other non-target alditols being sent to hydrogenolysis for glycol production. Partial recovery of target alditols such as xylitol or sorbitol and not requiring high performance, high recovery separation scenarios (greater than 75-90% for xylitol or sorbitol, for example) dramatically reduces net alditol separations costs and yet optimizes total alditol and glycol yield. Thus, co-production of alditols and glycols facilitate net lower cost and higher output. Tables 2-B and 2-C illustrate hydrogenation basics of taking xylose and converting xylose to xylitol employing a sponge metal catalyst with a nickel content of about 50 to about 80%.

TABLE 2-A

Exemplary Process Conditions and Results of Glucose Hydrogenation

| Sample ID | LHSV (1/h) | Hydrogen Gas Flow (g/h) | Reactor Pressure (psi) | Average Temperature (C.°) | Feed pH | Product pH | Glucose In Feed (g/L) | Glucose Remaining (g/L) | Mannitol Created (g/L) | Sorbitol Created (g/L) | Total Feed Conversion (%) |
|---|---|---|---|---|---|---|---|---|---|---|---|
| J680 | 1.2 | 100 | 1162 | 109 | 9.9 | 5.0 | 214.1 | 1.2 | 10.5 | 199.9 | 99.4 |
| J700 | 1.4 | 125 | 1148 | 112 | 10.0 | 4.6 | 218.7 | 4.7 | 16.7 | 199.5 | 97.8 |
| J701 | 1.0 | 100 | 1764 | 110 | 9.9 | 4.9 | 218.5 | 0.3 | 15.8 | 194.6 | 99.9 |
| J743 | 1.2 | 100 | 1756 | 111 | 9.6 | 4.6 | 213.2 | 1.8 | 14.2 | 192.5 | 99.1 |

TABLE 2-B

Exemplary Process Conditions and Results of Xylose Hydrogenation

| Sample ID | LHSV (1/h) | Hydrogen Gas Flow (g/h) | Reactor Pressure (psi) | Average Temperature (C.°) | In Feed pH | Product pH | Xylose Feed (g/L) | Xylose Remaining (g/L) | Arabitol Created (g/L) | Xylitol Created (g/L) | Total Feed Conversion (%) |
|---|---|---|---|---|---|---|---|---|---|---|---|
| J753 | 1.0 | 110 | 1744 | 105 | 9.5 | 4.7 | 215.8 | 0.0 | 13.2 | 193.7 | 100.0 |
| J758 | 1.4 | 150 | 1760 | 105 | 9.5 | 4.8 | 215.0 | 0.3 | 13.2 | 194.6 | 100.0 |
| J771 | 1.4 | 150 | 1779 | 100 | 9.5 | 4.7 | 218.4 | 0.3 | 0.0 | 210.9 | 100.0 |
| J773 | 1.4 | 150 | 1782 | 100 | 9.5 | 4.8 | 218.4 | 0.3 | 0.0 | 210.9 | 100.0 |
| J776 | 1.4 | 150 | 1811 | 92 | 9.5 | 9.8 | 220.9 | 0.0 | 8.4 | 204.5 | 100.0 |
| J798 | 1.4 | 75 | 1801 | 91 | 8.5 | 5.2 | 216.9 | 3.1 | 4.2 | 203.2 | 98.6 |

TABLE 2-C

Exemplary Process Conditions and Results of Wheat Straw Sugar (Source 1) Hydrogenation

| Sample ID | LHSV (1/h) | Hydrogen Gas Flow (g/h) | Reactor Pressure (psi) | Average Temperature (C.°) | Feed pH | Product pH | Glucose In Feed (g/L) | Xylose In Feed (g/L) | Arabinose In Feed (g/L) |
|---|---|---|---|---|---|---|---|---|---|
| J799 | 1.4 | 75 | 1803 | 93 | 9.0 | 4.8 | 18.2 | 200.8 | 7.7 |
| J800 | 1.4 | 75 | 1797 | 94 | 9.0 | 4.8 | 18.2 | 200.8 | 7.7 |
| J801 | 1.4 | 75 | 1795 | 94 | 9.0 | 5.0 | 18.2 | 200.8 | 7.7 |
| J802 | 1.4 | 75 | 1793 | 88 | 9.0 | 5.4 | 18.2 | 200.8 | 7.7 |

| Sample ID | Galactose In Feed (g/L) | Mannose in Feed (g/L) | Glucose Remaining (g/L) | Xylose Remaining (g/L) | Arabitol/Mannitol Created (g/L) | Sorbitol Created (g/L) | Xylitol Created (g/L) | Total Feed Conversion (%) |
|---|---|---|---|---|---|---|---|---|
| J799 | 3.0 | 4.4 | 4.4 | 6.6 | 17.3 | 15.0 | 141.7 | 95.3 |
| J800 | 3.0 | 4.4 | 6.6 | 9.7 | 23.9 | 18.6 | 184.2 | 93.0 |
| J801 | 3.0 | 4.4 | 6.5 | 9.0 | 24.2 | 18.6 | 183.7 | 93.4 |
| J802 | 3.0 | 4.4 | 2.2 | 2.8 | 10.9 | 9.5 | 82.9 | 97.9 |

In summary, in the production of alditols there are two main products of interest (as discussed above for example sorbitol and xylitol). The main purpose of producing mixed alditols (with or without target alditols removed) is to provide a C5/C6 hydrogenolysis feedstock. Thus mixed alditols from hydrogenation can be a source of specific alditols (such as mannitol or arabitol) or alditols for hydrogenolysis to make high valued glycols.

Example 3. Selective Concentration of C5 Alditols Via Unit Operations

Upon C5/C6 sugar hydrogenation, the C5/C6 sugars in general regardless of C5/C6 ratio or the variability of various alditol C5/C6 isomers will result in 97-99% conversion of sugar aldoses to corresponding alditols. Alditol drift might alter slightly the isomeric compositions but overall conversion should be constant and high.

If, for example, xylitol is a target alditol then several process options would be possible for xylitol concentration and subsequent further purification to a liquid or crystallized product. First, in the case of lower xylitol concentrations such as xylitol less than 30% of the total C5/C6 alditols, classical and/or recent development in industrial chromatography including Simulated Moving Bed (SMB) technology could be employed. Depending on system configuration, resin types, elution and recycle loops, the concentration could move from 30% to 50% to 70%. In the other state-of-the-art processes chromatographic separation currently is entirely centered on driving maximum recovery of the target material and concentrating the materials. This dual criteria of high removal rates and high purity of fractions recovered is onerous in terms of operations and costs. More equipment is needed, higher recycle rates, high dilutions, etc. So 20-40% recovered in higher purities is considered acceptable. The intent is to purify and concentrate a fraction of the target alditols, but not necessitate total recovery. Downstream glycol production after hydrogenolysis serves as an ultimate value-added co-product to target alditols. Further by changing the physical from non-volatile alditols, which are difficult to separate, to volatile glycols which can be separated easily by distillation the overall net separation costs of alditols and glycols are lower. Likewise, sorbitol or mannitol (C6 alditols) could be targeted as the main product alditol.

Table 3 summarizes several alternative resin and SMB system configurations and resulting concentrations of xylitol and sorbitol from respective alditol mixes.

TABLE 3

Chromatographic Resin Systems for Concentrating C5 and C6 Alditols

| Feedstock | SMB A Resin #1 Elution Rate | SMB B Resin #2 Elution Rate | SMB C Resin #3 Elution Rate | SMB D Resin #4 Elution Rate | SMB E Resin #5 Elution Rate |
|---|---|---|---|---|---|
| 50% C5 alditols 50:50 X/A 50% C6 alditols 50:50 S/M | % Xylitol recovery 50% % Xylitol bypass to hydrotreating 50% | % Xylitol recovery 65% % Xylitol bypass to hydrotreating 35% | % Xylitol recovery 75% % Xylitol bypass to hydrotreating 25% | % Sorbitol recovery 40% % Sorbitol bypass to hydrotreating 60% | % Sorbitol recovery 55% % Sorbitol bypass to hydrotreating 45% |
| Estimated % Separation Capex 90% recovery = 1.00 or 100% | 0.4 | 0.6 | 0.75 | 0.6 | 0.8 |
| Estimated % Separation Opex 90% recovery = 1.00 or 100% | 0.3 | 0.5 | 0.8 | 0.6 | 0.8 |

X = xylitol,
A = arabitol,
S = sorbitol,
M = mannitol

Example 4. Alditol Concentration and Crystallization

Alditols (xylitol, arabinitol, sorbitol, mannitol and other epimer alditols) have a 25% solids in water maximum concentration after hydrogenation. This mix can be further concentrated by select moving bed chromatography with resins selected for retaining C6 alditols and concentrate C5 in the permeate and/or taking alditol at 25% and via reverse osmosis or other techniques water removal and/or by selectively converting for example arabinatol to xylitol. Higher concentrations of alditols with a higher xylitol percentage can be crystallized with or without the addition of antisolvents (e.g., ethanol) to facilitate crystallization.

Individual alditols have varying degrees of solubility in water with sorbitol and arabitol having the highest solubilities followed by xylitol and then mannitol at a given temperature. Further solubility is impacted by anti solvents such as ethanol/water mixtures used to solubilize alditols. The higher the ethanol concentration, the lower the alditol solubility. The combination of solubility differences and the possible use of ethanol in the extraction and crystallization stages makes it feasible to control product isolation.

Table 4-A summarizes the effect of xylitol concentration on xylitol crystallization. Table 4-B summarizes the effect of ethanol/water solvent volume on xylitol crystallization.

TABLE 4-A

Examples of Concentration of Xylitol Feedstock on Crystallization Yield

| Test | Crystal Seed % | Starting Xylitol Concentration g/liter | Xylitol after Evaporation g/liter | Total Crystallization Yield % | Purity Degree % |
|---|---|---|---|---|---|
| 1 | 1% | 65.86 | 632.33 | 45.32 | 98.47 |
| 2 | 1% | 73.73 | 691.98 | 52.43 | 97.32 |
| 3 | 1% | 79.99 | 750.00 | 60.02 | 95.00 |
| 4 | 1% | 73.73 | 908.27 | 74.74 | 80.77 |

TABLE 4-B

Effects of Ethanol/Water Volume on Xylitol Crystallization

| Test | Crystal Seed % | Ethanol/Water V:V | Crystallization after 24 hrs % | Crystallization after 48 hrs % | Purity Degree % |
|---|---|---|---|---|---|
| 1 | 1% | 1:3 | 87.33 | 95.35 | 63.48 |
| 2 | 1% | 1:2 | 83.44 | 90.66 | 66.52 |
| 3 | 1% | 1:1 | 52.67 | 56.67 | 69.82 |
| 4 | 1% | 0:1 | 23.53 | 37.78 | 97.57 |

The combination of producing a variety of specific C5/C6 alditols (xylitol or sorbitol) from a corresponding mixed C5/C6 aldose feedstock (xylitol, arabitol, mannitol, galactitol, sorbitol) allows for the combined staged use of water solubility versus a water/ethanol combined aldose with, for example, chromatography to concentrate xylitol or other alditols to suitable levels for extraction into a high purity cut. That purer cut can in turn be staged re-crystallized to make a series of higher (98% for example plus) purities.

In summary target alditols can be removed with the bulk of non-target alditols used for hydrogenolysis.

Example 5. Alditol Hydrogenolysis to Make Glycols

Table 5-A illustrates representative mixed alditols to glycols via hydrogenolysis. Note in the table that C5 xylitol for example makes more ethylene glycol (EG) (26%) than a corresponding C6 sorbitol feed EG (13%). Given that "green EG" used for renewable sustainable PET bottles is preferred in the market over conventional non-green EG, illustrates the flexibility of the process developed herein. A Propylene glycol (PG) focus would shift to a higher C6/C5 ratio. Resulting glycols PG, EG, GLY (glycerin) and BDs (butanediol isomers) can be separated by classical distillation and/or extractive and azeoptropic distillation.

solution was then added to a crystallization vessel at 5° C. The temperature of the vessel contents was monitored. At 30° C. xylitol (3 g) seed was added along with 100 ml of ethanol (95%). Solid xylitol was removed by filtration after 1 hour post seed. The data in Table 6 shows the effect of sorbitol and mannitol concentration on the purification of xylitol from the model systems.

Mannitol has a low solubility level. As is shown by the data in Table 6 at mannitol concentrations >10%, undesirable co-crystallization of mannitol with xylitol is observed. When the mannitol content was 4% w/w or less of the crystallization liquor, successful purification of xylitol was achieved.

It is also shown by the data in Table 6 that concentrations of sorbitol of >15% reduces the rate of xylitol crystallization and filtration speeds are also reduced.

TABLE 5-A

Representative Mixed Alditols to Glycols via Hydrogenolysis

|  | Sorbitol C6 | Xylitol C5 | 10% Galactitol; 12% Sorbitol; 23% Arabitol; 55% Xylitol | 60% Sorbitol 40% Mannitol | 75% Xylitol; Sorbitol 25% |
|---|---|---|---|---|---|
| Alditol Concentration (wt/wt %) | 25% | 22% | 21% | 21% | 25% |
| pH (Base) | 12.5 (NaOH) | 12.4 (NaOH) | 12.4 (NaOH) | 12.4 (NaOH) | 12.4 (NaOH) |
| Temp ° C. | 214 | 200 | 193 | 184 | 200 |
| Pressure psig | 1800 | 1700 | 1700 | 1700 | 1700 |
| LHSV (hr$^{-1}$) | 1.5 | 2 | 2 | 0.9 | 2 |
| H$_2$ (Molar ratio) | 8 | 8 | 8 | 8 | 8 |
| Yields based on mass: |  |  |  |  |  |
| PG %, | 33% | 33% | 30% | 21% | 31% |
| EG %, | 13% | 26% | 23% | 11% | 25% |
| Glycerol % | 1% | 10% | 11% | 22% | 10% |
| BDs % | ND | ND | ND | ND | ND |
| Catalyst | Ni/Cu on Zirconia | Ni/Cu on Cr-Zirconia | Ni/Cu on Cr-Zirconia | Ni/Cu on Cr-Zirconia | Ni/Cu on Cr-Zirconia |

Example 6. Effect of Sorbitol and Mannitol on the Purification of Xylitol

Model crystallization liquor system mixtures containing varying amounts of xylitol, mannitol, sorbitol, and other sugars were prepared by dissolving mixtures of alditols and aldoses in water at 85° C. to give a solution with a total solids composition in % w/w as indicated in Table 6. Each

TABLE 6

| Run No. | Total Solids (%) | Xylitol Input (% of Polyols) | Xylitol Yield (% of Input) | Purity (%) | Other polyols (%) | Comment | Input Polyol composition Sorbitol (S) (%):Mannitol (M) (%) and Galactitol (G) (%) (All containing 70% Xylitol) |
|---|---|---|---|---|---|---|---|
| 01120 | 60 | 70 | <5 | NA | NA | Very low yield | S(15%):M (15%) |
| 01118 | 60 | 70 | <5 | 55 | 45 | Only seed visible | S(20%):M (10%) |
| 01077 | 60 | 70 | 72 | 33 | 67 | No comment | S(0%):M (30%) |
| 00939-3 | 60 | 70 | No solid | N/A | N/A | No comment | S(30%):M (0%) |
| 00939-5 | 75 | 50 | No solid | N/A | N/A | No comment | S(40%):M (5%):G(5%) |
| 00939-7 | 75 | 50 | >100 | N/A | N/A | Very slow filtration | S(30%):M (15%):G(5%) |
| 00930 | 75 | 70 | 81 | N/A | N/A | Bulk crystallization - starts at 60° C. | S(0%):M (30%) |
| 00939-1 | 75 | 70 | 60 | N/A | N/A | Slow onset of crystallization - | S(30%):M (0%) |

TABLE 6-continued

| Run No. | Input Percentages | | | | | Input Polyol composition Sorbitol (S) (%):Mannitol (M) (%) and Galactitol (G) (%) (All containing 70% Xylitol) |
|---|---|---|---|---|---|---|
| | Total Solids (%) | Xylitol Input (% of Polyols) | Xylitol Yield (% of Input) | Purity (%) | Other polyols (%) | Comment |
| 00948 | 75 | 70 | 82 | 60 | 40 | filtered 2 hours post seed Very slow crystallization - overnight at 5° C. | S(15%):M (15%) |
| 00952 | 75 | 70 | 88 | N/A | N/A | Very slow crystallization - overnight at 5° C. | S(20%):M (10%) |
| 00939-7 | 75 | 50 | | N/A | N/A | Very slow crystallization | S (30%):M (15%):(5%) |
| 00939-9 | 80 | 52 | >100 | N/A | N/A | Bulk crystallization - difficult to filter etc | S (22%):M (20%):G (6%) |
| 00736 | 85 | 80 | >100 | N/A | N/A | Difficult to dry | S(5%):M (10%):G(5%) |
| 00737 | 85 | 80 | >100 | N/A | N/A | Difficult to filter and dry - exhibits some sheer thinning/ thixotropic behavior (qualitative observation) | S (5%):M (10%); G (5%) |

While the invention has been described with reference to an exemplary embodiment, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A process, comprising:
   deconstructing a plant biomass to form a mixed C5/C6 sugar stream;
   hydrolyzing the mixed C5/C6 sugar stream to form a mixed C5/C6 monomer sugar stream;
   selecting a target alditol or a target blend of alditols,
   hydrogenating continuously the mixed C5/C6 monomer sugar stream to form a mixed C5/C6 alditol stream;
   isolating the target alditol or target blend of alditols from the mixed C5/C6 alditol stream to leave a residual mixed C5/C6 alditol stream, wherein the isolating the target alditol or target blend of alditols comprises crystallization;
   continuous hydrogenolysis of the residual mixed C5/C6 alditol stream to form a mixed C2-C4 glycol stream; and
   isolating a target glycol or target blend of glycols from the mixed C2-C4 glycol stream;
   wherein at least 10% of the overall target product yield is either target alditol/target blend of alditols or target glycol/target blend of glycols.

2. The process of claim 1, wherein the mixed C5/C6 monomer sugar stream comprises greater than or equal to 60% of a C5 monomer sugar based on a combined total of C5 and C6 monomer sugars; or
   wherein the mixed C5/C6 monomer sugar stream comprises greater than or equal to 60% of a C6 monomer sugar based on a combined total of C5 and C6 monomer sugars.

3. The process of claim 1, further comprising, prior to hydrogenating, adjusting the mixed C5/C6 monomer sugar stream to a targeted C5 to C6 monomer sugar ratio by adding a source of C5 monomer, C6 monomer, or a combination thereof.

4. The process of claim 1, wherein the hydrogenating is conducted on the mixed C5/C6 monomer sugar stream comprising about 20 to about 25% w/w total sugars in water and having a pH of about 7 to about 13, wherein the hydrogenating is conducted at a LHSV of about 0.41 to about 3.5, a hydrogen pressure of about 600 to about 2000 psig, about 3 to about 10 times stoichiometric hydrogen, and a temperature of about 105 to about 150° C., and has a 99% or more C5/C6 monomer sugar to alditol conversion.

5. The process of claim 1, wherein the target alditol is xylitol and is crystallized from a solution having a total dissolved solids content of about 40% to about 80% w/w.

6. The process of claim 1, wherein the target alditol is xylitol and is crystallized from a solution having a xylitol content as % of total solids of the crystallization solution of 50% or more; an amount of arabitol as % of total solids of the crystallization solution of less than or equal to 10%; mannitol as % of total solids of the crystallization solution of less than or equal to 10%; and sorbitol as % of total solids of the crystallization solution of less than or equal to 15%.

7. The process of claim 1, wherein the target alditol is xylitol or sorbitol.

8. The process of claim 1, further comprising, prior to isolating the target alditol from the mixed C5/C6 alditol stream, adjusting the mixed C5/C6 alditol stream to a targeted C5 to C6 alditol ratio by adding a source of C5 alditol, C6 alditol, or a combination thereof.

9. The process of claim 1, wherein the hydrogenolysis is conducted on the residual mixed C5/C6 alditol stream having about 20 to about 25% w/w total solids content of alditol in water, a pH of about 7 to about 13, a LHSV of about 0.4 to about 4.0, a hydrogen pressure of about 1200 to about 2000 psig, a temperature of about 190 to about 250° C. in the presence of a nickel based catalyst to form the mixed C2-C4 glycol stream comprising propylene glycol, ethylene glycol, glycerin, butanediol isomers, or a combination thereof.

10. The process of claim 1, wherein the mixed C2-C4 glycol stream comprises about 15% to about 50% propylene glycol, about 15% to about 40% ethylene glycol, about 10% to about 40% glycerin, and about 5% to about 30% butanediol isomers, all amounts in % by weight of the total weight of the mixed glycol stream.

11. The process of claim 1, wherein the mixed C5/C6 monomer sugar stream is derived from a hydrolyzed biomass.

12. The process of claim 11, wherein the biomass is bagasse (sugarcane bagasse, sorghum bagasse, sugarbeet pulp), corn cobs, corn husks, corn stover, grain straw (barley, oat, rice, wheat), grasses (switch grass), hardwoods (birch, poplar, alder, eucalyptus), plant leaves, plant stalks, softwoods (cedar, hemlock, pine, spruce), sulfite pulp liquor, xylans from algae polysaccharides, or a combination thereof.

13. The process of claim 11, wherein the biomass is deconstructed by supercritical and hydrothermal degradation, alkaline hydrolysis, acid hydrolysis, enzymatic hydrolysis, or a combination of acid and enzymatic hydrolysis.

14. The process of claim 13, wherein deconstruction of the biomass forms pulp and a biomass hydrolysate stream comprising sugar monomers, cellulose, glucose, hemicellulose, hemicellulose based oligomeric compounds, solubilized lignin, and impurities.

15. The process of claim 11, wherein a cellulose to glucose sugar mass from the deconstruction of the biomass is removed via classical fermentation of glucose to ethanol by non-GMO yeast concentrating C5 non-fermentable sugars.

16. The process of claim 15, further comprising selectively removing cellulose from the biomass hydrolysate stream to result in a lignin and mixed C5/C6 sugar rich stream; or
further comprising selectively removing cellulose from the biomass hydrolysate stream to result in a lignin rich and mixed C5/C6 sugar rich stream where the C5 to C6 ratio of sugars is 75%-25% compared to the ordinary biomass ratio of C5/C6 at 15-20%; and
further comprising removing the lignin from the lignin and C5/C6 sugar rich stream to form a C5/C6 sugar rich stream.

17. The process of claim 16, further comprising hydrolyzing the C5/C6 sugar rich stream to form the mixed C5/C6 monomer sugar stream.

18. The process of claim 1, further comprising conditioning the mixed C5/C6 monomer sugar stream to remove non-sugar organic compounds and inorganic contaminants to form a conditioned C5/C6 monomer sugar stream that is then subjected to the hydrogenating step.

19. The process of claim 1, comprising
deconstructing wheat straw or deconstructing hemlock, alder, or a combination thereof, using alkaline conditions or an enzymatic process to form a mixed C5/C6 sugar stream;
conditioning the mixed C5/C6 sugar stream to remove lignin, organic impurities and inorganic impurities; and
hydrolyzing the mixed C5/C6 sugar stream under acidic conditions to form a mixed C5/C6 monomer sugar stream that is subject to the hydrogenation step;
wherein the target alditol is xylitol and the target glycol is propylene glycol; and
wherein xylitol is isolated by crystallization optionally with ethanol or isopropanol antisolvent.

* * * * *